United States Patent
Xu et al.

(10) Patent No.: US 11,946,036 B2
(45) Date of Patent: *Apr. 2, 2024

(54) BACTERIUM AND OBTAINING METHOD AND APPLICATION THEREOF

(71) Applicant: Shanghai Jiao Tong University, Shanghai (CN)

(72) Inventors: Ping Xu, Shanghai (CN); Bo Xin, Shanghai (CN); Fei Tao, Shanghai (CN); Yu Wang, Shanghai (CN); Hongzhi Tang, Shanghai (CN); Cuiqing Ma, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/671,001

(22) Filed: Feb. 14, 2022

(65) Prior Publication Data

US 2022/0162546 A1    May 26, 2022

Related U.S. Application Data

(63) Continuation of application No. 16/317,790, filed as application No. PCT/CN2017/093235 on Jul. 17, 2017, now Pat. No. 11,248,206.

(30) Foreign Application Priority Data

Jul. 15, 2016  (CN) .......................... 201610561771.7

(51) Int. Cl.
*C12N 1/20*    (2006.01)
*C12N 9/02*    (2006.01)
(Continued)

(52) U.S. Cl.
CPC ............. *C12N 1/20* (2013.01); *C12N 9/0006* (2013.01); *C12N 9/0008* (2013.01); *C12N 9/001* (2013.01);
(Continued)

(58) Field of Classification Search
CPC ................ C12N 9/0006; C12N 9/0008; C12N 9/1022; C12N 9/1217; C12N 15/52
See application file for complete search history.

(56) References Cited

FOREIGN PATENT DOCUMENTS

| CN | 1276962 C | 9/2006 |
|---|---|---|
| CN | 101173242 A | 5/2008 |

(Continued)

OTHER PUBLICATIONS

International Search Report of the State Intellectual Property Office of the Peoples Republic of China dated Oct. 11, 2017 for International Application No. PCT/CN2017/093235 and English Translation, 10 pages.

(Continued)

*Primary Examiner* — Yong D Pak
(74) *Attorney, Agent, or Firm* — Fitch, Even, Tabin & Flannery, LLP

(57) ABSTRACT

The present invention discloses a bacterium and an obtaining method and application thereof. The bacterium has a property of coproducing 1,3-propanediol and D-lactic acid. Further, the bacterium is *Klebsiella oxytoca*, including *Klebsiella oxytoca* PDL-5 CCTCC M 2016185. The obtaining method of the bacterium may be to obtain the bacterium by directly screening wild bacteria that satisfy conditions from the environment or performing gene engineering modification to wild bacteria. The present invention has the advantages that the bacteria can coproduce 1,3-propanediol and D-lactic acid through fermentation, the molar conversion rate and the concentration of the two products are very high, (Continued)

the types of byproducts are few, the concentration is low, the product extraction process is simplified, the high-efficiency biological production of 1,3-propanediol and D-lactic acid can be realized, and the industrial application prospect is very great.

4 Claims, 2 Drawing Sheets

Specification includes a Sequence Listing.

(51) Int. Cl.
*C12N 9/04* (2006.01)
*C12N 9/06* (2006.01)
*C12N 9/10* (2006.01)
*C12N 9/12* (2006.01)
*C12N 9/88* (2006.01)
*C12N 1/02* (2006.01)
*C12P 7/18* (2006.01)
*C12P 7/56* (2006.01)
*C12R 1/22* (2006.01)
*C12R 1/25* (2006.01)

(52) U.S. Cl.
CPC ......... *C12N 9/1022* (2013.01); *C12N 9/1217* (2013.01); *C12N 9/88* (2013.01); *C12N 1/02* (2013.01); *C12N 1/205* (2021.05); *C12P 7/18* (2013.01); *C12P 7/56* (2013.01); *C12R 2001/22* (2021.05); *C12R 2001/25* (2021.05); *C12Y 101/01001* (2013.01); *C12Y 101/01004* (2013.01); *C12Y 101/01028* (2013.01); *C12Y 101/01076* (2013.01); *C12Y 101/01202* (2013.01); *C12Y 203/01054* (2013.01); *C12Y 207/0104* (2013.01); *C12Y 401/03001* (2013.01); *C12Y 402/0103* (2013.01)

(56) References Cited

FOREIGN PATENT DOCUMENTS

| CN | 100554405 | | 10/2009 |
|---|---|---|---|
| CN | 102304551 | A | 1/2012 |
| CN | 102321680 | A | 1/2012 |
| CN | 101144086 | B | 9/2012 |
| CN | 102952826 | A | 3/2013 |
| CN | 102690764 | B | 7/2013 |
| CN | 103298945 | A | 9/2013 |
| CN | 103305543 | A | 9/2013 |
| CN | 103756939 | A | 7/2015 |
| CN | 106190901 | A | 12/2016 |
| CN | 106190936 | A | 12/2016 |
| WO | 96/35796 | A1 | 11/1996 |
| WO | 2012/062832 | A1 | 5/2012 |
| WO | 2012/167525 | A1 | 12/2012 |

OTHER PUBLICATIONS

Feng, Xinjun et al., "Production of optically pure D-lactate from glycerol by engineered Klebsiella pneumoniae strain," Bioresource Technology, Nov. 2014, vol. 172, pp. 269-275.
Genbank, JH603143.1, frdA and poxB, 2015, Klebsiella oxytoca 10-5243 genomic scaffold supercont1.1, whole genome shotgun sequence, and GenBank, JH603144.1, 2015, Klebsiella oxytoca 10-5243 genomic scaffold supercont1.2, whole genome shotgum sequence, 4 pages.
Jiang, Jingwei et al., "Complete genome sequence and comparative genome analysis of Klebsiella oxytoca HKOPL1 isolated from giant panda feces," BMC Research Notes, Nov. 2014, vol. 7, No. 827, pp. 1-11.
Sangproo, Maytawadee et al., "Metabolic engineering of Klebsiella oxytoca M5a1 to produce optically pure D-actate in mineral salts medium," Bioresource Technology, 119, 2012, pp. 191-198.
Shin, Sang Heum et al., "Complete Genome Sequence of Klebsiella oxytoca KCTC 1686, Used in Production of 2,3-Butanediol," Journal of Bacteriology, Dec. 2012, pp. 2371-2372.
Tian, Kangming et al., "High-efficiency conversion of glycerol to D-Lactic acid with metabolically engineered *Escherichia coli*," African Journal of Biotechnology, Mar. 2012, vol. 11, No. 21, pp. 4860-4867.
Wang, Yu et al., "Glycerol Dehydrogenase Plays a Dual Role in Glycerol Metabolism and 2,3-Butanediol Formation in Klebsiella pneumoniae," Journal of Biological Chemistry, Feb. 2014, vol. 289, No. 9, pp. 6080-6090.
Wilson, Kate J. et al., "β-Glucuronidase (GUS) transposons for ecological and genetic studies of rhizobia and other Gram-negative bacteria," Microbiology, Jul. 1995, vol. 141, pp. 1961-1705.
WO 2012/167525 A1, Machine Translation via https://ipportal.wipo.int/ on Oct. 6, 2020.
Xu, Yun-Zhen et al., "Metabolism in 1,3-Propanediol Fed-Batch Fermentation by a D-Lactate Deficient Mutant of Klebsiella pneumoniae," Biotechnology and Bioengineering, Dec. 2009, vol. No. 5, pp. 965-972.
Zhang, Huizhai, editor, "Pathway Engineering: The Third Generation of Genetic Engineering," China Light Industry Press, Jan. 2002, pp. 110-111, and English Abstract, 2 pages.
Zhang, Gang et al., "Influence of Blocking of 2,3-Butanediol Pathway on Glycerol Metabolism for 1,3-Propanediol Production by Klebsiella oxytoca," Appl Biochem Biotechnol, 2012, vol. 168, pp. 116-128.
Zhou, Li et al., "Evaluation of Genetic Manipulation Strategies on D-Lactate Production by *Escherichia coli*," Current Microbiology, Nov. 2010, vol. 62, Issue 3, pp. 981-989.

BACTERIUM AND OBTAINING METHOD AND APPLICATION THEREOF

CROSS-REFERENCE TO RELATED APPLICATIONS

This application is a continuation of prior application Ser. No. 16/317,790, filed Jan. 14, 2019, which is a U.S. national phase application filed under 35 U.S.C. § 371 of International Application Number PCT/CN2017/093235, filed Jul. 17, 2017, designating the United States, which claims priority from Chinese Patent Application Number 201610561771.7, filed Jul. 15, 2016.

REFERENCE TO A SEQUENCE LISTING

The Sequence Listing associated with this application is filed in electronic format via EFS-Web and is hereby incorporated into the specification in its entirety. The name of the text file containing the Sequence Listing is "01335-17108PIUS Sequence Listing." The size of the text file is 22.7 KB, and the text file was created on Mar. 7, 2019.

FIELD OF THE INVENTION

The present invention belongs to the field of biological engineering, and relates to a bacterium, and an obtaining method and application thereof. Here, the method for obtaining the bacterium comprises a method for constructing an artificial bacterium and a method for screening a wild bacterium.

DESCRIPTION OF THE PRIOR ART

Petroleum base polymers bring a very great convenience to production life of people. However, with the continuous decrease of petrochemical resources and the occurrence of the environmental problem caused by use of petrochemical resources, it is increasingly concerned to find new environmental-friendly non-petroleum base polymers. Biology base materials have advantages such as degradability, wide raw material source and easiness in chemical improvement, and thus they are greatly applied in many fields. At present, polytrimethylene terephthalate (PTT) and polylactic acid (PLA) are two biology base materials which are greatly concerned. PTT is a novel polyester fiber having excellent performance and is formed by terephthalic acid and 1,3-propanediol (1,3-PD) through polycondensation, and it integrates the advantages of Polyethylene terephthalate (PET) and polybutylene terephthalate (PBT), has features of very good softness, fluffiness, stain resistance, elasticity and ability of being dyed at normal temperature, and can be widely applied to various fields such as costume, decoration and engineering plastic. PLA is also called as polylactide and is a polymer obtained by using lactic acid (LAC) as a main raw material through polymerization, and it has good thermal stability, solvent resistance and biocompatibility, can be processed in many ways, can be used for manufacturing packaging materials, fibers and nonwoven fabrics, and is widely used in fields such as costume, buildings, agriculture and medical health. Besides, PLA products have good biodegradability, can be fully degraded by microbes in nature after use and are well-recognized environmental-friendly materials.

Huge market demands for biology base materials PTT and PLA facilitate the development of production of biology base material monomers 1,3-PD and optically pure LAC through biological processes. At present, methods for producing 1,3-PD through biological processes are mainly divided into two types, wherein the first type is to produce 1,3-PD (such as CN201110093628; ZL200710104008) by using gene engineering *Escherichia coli* and using saccharides such as glucose as a substrate; and the second type is to produce 1,3-PD (such as ZL200410100479; CN201180064621) by using intestinal bacteria and using glycerol as a substrate. Recently, due to development of biological diesel industry, the price of glycerol as a byproduct gradually decreases and glycerol is an ideal substrate for producing 1,3-PD. Strains capable of producing 1,3-PD by using glycerol mainly include *Klebsiella pneumoniae, Klebsiella oxytoca, Citrobacter freundii, Clostridium butyricum* and the like. LAC used for producing PLA must have high optical purity, and thus researchers screen and obtain many bacteria capable of producing optically pure LAC, for example, wild bacteria such as *Lactobacillus rhamnosus, Bacillus coagulans* and *Sporolactobacillus terrae*, which can produce high-concentration optically pure L-lactic acid (L-LAC) and D-lactic acid (d-LAC) by using saccharides as raw materials (ZL200710176057; ZL201210115365; CN201410022868).

By using the above-mentioned strains and production methods, production of one compound of 1,3-PD and LAC through biological processes can be realized. However, at present, there is no strain capable of simultaneously producing 1,3-PD and optically pure LAC (L-LAC or D-LAC). *Klebsiella pneumoniae* and *Klebsiella oxytoca* will further produce a small amount of byproducts such as 2,3-butanediol, ethanol, LAC, succinic acid, acetic acid and formic acid in a process of producing 1,3-PD by using glycerol as a substrate. Although fermentation solution obtained by fermentation of glycerol through the two strains simultaneously contain 1,3-PD and LAC, since the difference in concentration of the two compounds is great (generally is not of the same order of magnitude, consequently one of compounds can only be treated as a byproduct. Moreover, since alcohol products and acid products are various, the components are complex and it is difficult to separate to obtain high-purity LAC, simultaneous production of 1,3-PD and LAC cannot be realized. In industrial large-scale production, factors such as product concentration, conversion rate and extraction cost must be considered. If simultaneous production of 1,3-PD and optically pure LAC (L-LAC and D-LAC) at high conversion rate by using one strain can be realized by using glycerol as a substrate and taking 1,3-PD and optically pure LAC (L-LAC and D-LAC) as main products, the production cost will be greatly reduced and the production efficiency will be improved.

SUMMARY OF THE INVENTION

Aiming at the defects of the prior art, the present invention provides a bacterium, and the bacterium has a property of coproducing 1,3-propanediol and D-lactic acid. Coproducing refers to simultaneously production.

Further, the bacterium is an artificial bacterium obtained through modification of a wild bacterium.

Further, the wild bacterium has the following metabolic pathways:

1) glycerol→1,3-propanediol; and/or
2) glycerol→pyruvic acid→D-lactic acid;

the wild bacterium further has one or more of the following metabolic pathways:

3) pyruvic acid→α-acetolactic acid, α-acetolactate synthetase (budB) being an enzyme for catalyzing the metabolic pathway;

4) α-acetolactic acid→acetoin, α-acetolactate decarboxylase (budA) being an enzyme for catalyzing the metabolic pathway;

5) pyruvic acid→acetic acid, pyruvate oxidase (poxB) being an enzyme for catalyzing the metabolic pathway;

6) acetyl coenzyme A→acetyl phosphate, acetyl phosphate transferase (pta) being an enzyme for catalyzing the metabolic pathway;

7) acetyl phosphate→acetic acid, acetokinase (ackA) being an enzyme for catalyzing the metabolic pathway;

8) acetyl coenzyme A→acetaldehyde, aldehyde dehydrogenase (adhE) being an enzyme for catalyzing the metabolic pathway; and 9) fumaric acid→succinic acid, fumarate reductase (frdA) being an enzyme for catalyzing the metabolic pathway; and the modification comprises: blocking one or more of the metabolic pathways 3)-9).

Further, the wild bacterium is *Klebsiella oxytoca*.

Further, the wild bacterium is *Klebsiella oxytoca* PDL-0, the *Klebsiella oxytoca* PDL-0 was collected in China Center for Type Culture Collection on Apr. 8, 2016, and the collection registration number is CCTCC M 2016184.

Further, the modification comprises: blocking one or more of the metabolic pathways 3)-9) by inhibiting or removing the activity of the enzyme.

Further, the modification comprises: inhibiting or removing the activity of the enzyme by changing genes of the enzyme.

Further, the modification comprises: changing the genes of the enzyme by adopting a gene recombination method.

Further, a sequence for coding an α-acetolactate decarboxylase gene is expressed as SEQ ID NO:1;

a sequence for coding an α-acetolactate synthetase gene is expressed as SEQ ID NO:2;

a sequence for coding an aldehyde dehydrogenase gene is expressed as SEQ ID NO:3;

a sequence for coding acetokinase and acetyl phosphate transferase genes is expressed as SEQ ID NO:4;

a sequence for coding a pyruvate oxidase gene is expressed as SEQ ID NO:5; and a sequence for coding a fumarate reductase gene is expressed as SEQ ID NO:6.

Further, one or more genes of budA, budB, adhE, ackA-pta, poxB and frdA of the artificial bacterium are defected.

In one preferred embodiment, genes budA and budB of the artificial bacterium are defected.

In another preferred embodiment, genes budA, budB and adhE of the artificial bacterium are defected.

In another preferred embodiment, genes budA, budB, adhE and ackA-pta of the artificial bacterium are defected.

Further, the gene defects are produced by adopting a homologous recombination method.

Further, a genotype of the artificial bacterium comprises ΔbudA ΔbudB ΔadhE ΔackA-pta ΔpoxB ΔfrdA. ΔbudA ΔbudB ΔadhE ΔackA-pta ΔpoxB ΔfrdA expresses defects or mutations of the α-acetolactate decarboxylase gene (budA), α-acetolactate synthetase gene (budB), aldehyde dehydrogenase gene (adhE), acetokinase and acetyl phosphate transferase genes (ackA-pta), pyruvate oxidase gene (poxB) and fumarate reductase gene (frdA).

Preferably, a genotype of the artificial bacterium comprises ΔbudA ΔbudB ΔadhE ΔackA-pta ΔpoxB ΔfrdA.

To describe from another angle, the artificial bacterium is obtained by defecting budA, budB, adhE, ackA-pta, poxB and frdA genes of the wild bacterium; and the artificial bacterium produces 1,3-PD and D-LAC, and a total conversion rate of 1,3-PD and D-LAC exceeds 90%. A total conversion rate calculation formula is as follow: total conversion rate=molar conversion rate of 1,3-PD+ molar conversion rate of D-LAC, where molar conversion rate of 1,3-PD=(final concentration of 1,3-PD*volume of final fermentation solution*molar mass 92 of glycerol)/(mass of consumed glycerol*molar mass 76 of 1,3-PD); and molar conversion rate of D-LAC=(final concentration of D-LAC*volume of final fermentation solution*molar mass 92 of glycerol)/(mass of consumed glycerol*molar mass 90 of D-LAC).

Further, budA, budB, adhE, ackA-pta, poxB and frdA gene defects are obtained by adopting a homologous recombination method, and there is no fixed sequence for obtaining the gene defects; the homologous recombination method comprises amplifying upstream homologous segments and downstream homologous segments of the genes through PCR amplification, constructing the upstream homologous segments and the downstream homologous segments into suicide plasmids and transforming into *Escherichia coli* to obtain a donor; and performing biparental hybridization to the donor and a corresponding receptor to enable the upstream homologous segments and the downstream homologous segments to experience homologous recombination with a genome of the receptor to obtain a strain with the gene defects, i.e., the artificial bacterium.

Preferably, the wild bacterium is *Klebsiella oxytoca* PDL-0, the *Klebsiella oxytoca* PDL-0 was collected in China Center for Type Culture Collection on Apr. 8, 2016, and the collection registration number is CCTCC M 2016184.

Further, a DNA sequence of the budA is as expressed by SEQ ID NO:1; and/or a DNA sequence of the budB is as expressed by SEQ ID NO:2; and/or a DNA sequence of the adhE is as expressed by SEQ ID NO:3; and/or a DNA sequence of the ackA-pta is as expressed by SEQ ID NO:4; and/or a DNA sequence of the poxB is as expressed by SEQ ID NO:5; and/or a DNA sequence of the frdA is as expressed by SEQ ID NO:6.

In one preferred embodiment, the modification comprises introducing an exogenous 1,3-PD synthesis pathway and/or D-LAC synthesis pathway into the wild bacterium.

Further, the step of introducing the exogenous 1,3-PD synthesis pathway comprises transforming a glycerol dehydratase coding gene dhaB and a 1,3-PD oxidoreductase coding gene dhaT into the wild bacterium.

Further, the step of introducing the exogenous D-LAC synthesis pathway comprises performing codon optimization applicable to expression of the wild bacterium to a gene dldh$_{Bc}$ of D-lactate dehydrogenase and replacing the D-lactate dehydrogenase into a position of D-lactate dehydrogenase in a genome of the wild bacterium by using a shuttle plasmid, so as to realize constitutive expression of dldh$_{Bc}$ on the genome of the wild bacterium.

Further, the exogenously introduced gene dldh$_{Bc}$ of D-lactate dehydrogenase comes from *Bacillus coagulans* 2-6. *Bacillus coagulans* 2-6 is *Bacillus coagulans* CASH in CN101173242A and the collection number is CGMCC No2184.

Further, the wild bacterium is *Escherichia coli*. Preferably, the wild bacterium is *Escherichia coli* K12.

Further, the modification further comprises: changing budA, budB, adhE, ackA-pta, poxB and/or frdA genes by adopting a gene recombination method.

A situation that the bacterium requested to be protected by the present invention is an artificial bacterium is described.

In fact, the bacterium requested to be protected by the present invention may also be a wild bacterium, i.e., the bacterium is a wild bacterium.

Further, the bacterium is *Klebsiella oxytoca*.

Preferably, the bacterium is *Klebsiella oxytoca* PDL-0, the *Klebsiella oxytoca* PDL-0 was collected in China Center for Type Culture Collection on Apr. 8, 2016, and the collection registration number is CCTCC M 2016184.

In one preferred embodiment, the bacterium is *Klebsiella oxytoca* PDL-5, the *Klebsiella oxytoca* PDL-5 was collected in China Center for Type Culture Collection on Apr. 8, 2016, and the collection registration number is CCTCC M 2016185.

No matter that the bacterium is a wild bacterium or an artificial bacterium, the bacterium provided by the present invention has the following metabolic pathways:

1) glycerol→1,3-propanediol; and
2) glycerol→pyruvic acid→D-lactic acid.

The bacterium provided by the present invention has a property of coproducing 1,3-propanediol and D-lactic acid, wherein in products obtained through coproduction, a molar conversion rate of 1,3-propanediol is greater than or equal to 36.5%; and a molar conversion rate of D-lactic acid is greater than or equal to 39.0%.

Further, in products obtained through coproduction, the molar conversion rate of D-lactic acid is greater than or equal to 52.7%.

Further, in products obtained through coproduction, the molar conversion rate of 1,3-propanediol is greater than or equal to 40%.

Further, in products obtained through coproduction, the molar conversion rate of D-lactic acid is greater than or equal to 54.0%.

Further, in products obtained through coproduction, the molar conversion rate of 1,3-propanediol is greater than or equal to 42.6%; and the molar conversion rate of D-lactic acid is greater than or equal to 52.8%.

The bacterium provided by the present invention has a property of coproducing 1,3-propanediol and D-lactic acid, wherein in products obtained through coproduction, a total conversion rate of 1,3-propanediol and D-lactic acid exceeds 90%.

The bacterium provided by the present invention has a property of coproducing 1,3-propanediol and D-lactic acid, wherein a mass ratio of 1,3-propanediol to D-lactic acid obtained through coproduction is 1:0.1-10. Further, the mass ratio of 1,3-propanediol to D-lactic acid obtained through coproduction is 1:0.2-5. Preferably, the mass ratio of 1,3-propanediol to D-lactic acid obtained through coproduction is 1:0.5-2.

Further, the bacterium provided by the present invention comes from *Aspergillus, Saccharomyces, Zygosaccharomyces, Pichia, Kluyveromyces, Candida, Hansenula, Debaryomyces, Mucor, Torulopsis* or *Streptomyces* of fungi; or comes from *Methylovorus, Salmonella, Bacillus, Pseudomonas, Klebsiella, Lactobacillus, Enterobacter, Citrobacter, Pelobacter, Ilyobacter* or *Fusobacterium* of bacteria.

The present invention further discloses a method for constructing the bacterium, comprising the following steps:

step 1: screening *Klebsiella oxytoca* capable of producing 1,3-propanediol and D-lactic acid from a soil sample; and step 2: enabling one or more genes of budA, budB, adhE, ackA-pta, poxB and frdA of the *Klebsiella oxytoca* obtained in the step 1 to be defected to obtain the bacterium.

Further, the *Klebsiella oxytoca* obtained in the step 1 is *Klebsiella oxytoca* PDL-0, the *Klebsiella oxytoca* PDL-0 was collected in China Center for Type Culture Collection on Apr. 8, 2016, and the collection registration number is CCTCC M 2016184.

Further, a DNA sequence of the budA is as expressed by SEQ ID NO:1; a DNA sequence of the budB is as expressed by SEQ ID NO:2; a DNA sequence of the adhE is as expressed by SEQ ID NO:3; a DNA sequence of the ackA-pta is as expressed by SEQ ID NO:4; a DNA sequence of the poxB is as expressed by SEQ ID NO:5; a DNA sequence of the frdA is as expressed by SEQ ID NO:6.

Further, the step 2 comprises the following steps:

step 2-1: enabling a α-acetolactate decarboxylase gene and a α-acetolactate synthetase gene of the *Klebsiella oxytoca* PDL-0 CCTCC M 2016184 to be defected to obtain a strain with of the activities of α-acetolactate decarboxylase and α-acetolactate synthetase, which is named as *Klebsiella oxytoca* PDL-1;

step 2-2: enabling an aldehyde dehydrogenase gene of the *Klebsiella oxytoca* PDL-1 to be defected to obtain a strain losing the activity of aldehyde dehydrogenase, which is named as *Klebsiella oxytoca* PDL-2;

step 2-3: enabling acetokinase and acetyl phosphate transferase genes of the *Klebsiella oxytoca* PDL-2 to be defected to obtain a strain losing the activities of acetokinase and acetyl phosphate transferase, which is named as *Klebsiella oxytoca* PDL-3;

step 2-4: enabling a pyruvate oxidase gene of the *Klebsiella oxytoca* PDL-3 to be defected to obtain a strain losing the activity of pyruvate oxidase, which is named as *Klebsiella oxytoca* PDL-4; and step 2-5: enabling a fumarate reductase gene of the *Klebsiella oxytoca* PDL-4 to be defected to obtain a strain losing the activity of fumarate reductase, which is named as *Klebsiella oxytoca* PDL-5;

a sequence of the α-acetolactate decarboxylase gene is expressed as SEQ ID NO:1; a sequence of the α-acetolactate synthetase gene is expressed as SEQ ID NO:2; a sequence of the aldehyde dehydrogenase gene is expressed as SEQ ID NO:3; a sequence of the acetokinase and acetyl phosphate transferase genes is expressed as SEQ ID NO:4; a sequence of the pyruvate oxidase gene is expressed as SEQ ID NO:5; and a sequence of the fumarate reductase gene is expressed as SEQ ID NO:6.

Further, in the step 2, enabling the α-acetolactate decarboxylase gene, the α-acetolactate synthetase gene, the aldehyde dehydrogenase gene, the acetokinase and acetyl phosphate transferase genes, the pyruvate oxidase gene and the fumarate reductase gene of the *Klebsiella oxytoca* obtained in the step 1 to be defected comprises amplifying upstream homologous segments and downstream homologous segments of the genes through PCR amplification, constructing the upstream homologous segments and the downstream homologous segments into suicide plasmids and transforming into *Escherichia coli* to obtain a donor; and performing biparental hybridization to the donor and a corresponding receptor to enable the upstream homologous segments and the downstream homologous segments to experience homologous recombination with a genome of the receptor to obtain a strain with the gene defects, i.e., the bacterium.

Further, the suicide plasmids comprise suicide plasmids pKR6K; the *Escherichia coli* comprises *Escherichia coli* S17-1(λpir); the donor comprises *Klebsiella oxytoca* PDL-0 CCTCC M 2016184, *Klebsiella oxytoca* PDL-1, *Klebsiella oxytoca* PDL-2 and *Klebsiella oxytoca* PDL-3; and the receptor comprises *Klebsiella oxytoca* PDL-1, *Klebsiella oxytoca* PDL-2, *Klebsiella oxytoca* PDL-3 and *Klebsiella oxytoca* PDL-4.

The present invention further provides a method for constructing the bacterium, characterized in that an exogenous 1,3-PD synthesis pathway and/or an exogenous D-LAC synthesis pathway are introduced into a strain through gene engineering modification. The strain may be a strain producing 1,3-PD and/or D-LAC, and may also be a strain not producing 3-PD and/or D-LAC. The purpose of exogenously adding the 1,3-PD synthesis pathway and/or the exogenous D-LAC synthesis pathway is to enable the modified strain to produce 1,3-PD and/or D-LAC, or enable the yields of produced 1,3-PD and/or D-LAC to be higher.

Further, the step of introducing the exogenous 1,3-PD synthesis pathway refers to transforming a glycerol dehydratase coding gene dhaB and a 1,3-PD oxidoreductase coding gene dhaT into the strain through a plasmid to obtain a strain A which produces 1,3-PD.

Further, the step of introducing the exogenous 1,3-PD synthesis pathway refers to selecting a glycerol dehydratase coding gene dhaB and a 1,3-PD oxidoreductase coding gene dhaT in a 1,3-PD synthesis pathway in *Klebsiella oxytoca*, performing PCR cloning, then linking to a plasmid DNA pet-Duet and transforming into the strain to obtain a strain A which produces 1,3-PD.

Further, the step of introducing the exogenous D-LAC synthesis pathway refers to transforming a gene $dldh_{Bc}$ of D-lactate dehydrogenase into the strain through a plasmid to obtain a strain B which produces D-LAC.

Further, the step of introducing the exogenous D-LAC synthesis pathway refers to selecting a gene dldhBc for coding D-lactate dehydrogenase coming from *Bacillus coagulans* 2-6, performing codon optimization applicable to expression of the strain, and replacing the D-lactate dehydrogenase into a position of D-lactate dehydrogenase in a genome of the strain by using a shuttle plasmid to obtain a strain B which produces D-LAC.

Further, the method for constructing the bacterium further comprises the following operation: producing a strain with budA, budB, adhE, ackA-pta, poxB and/or frdA gene defects by adopting a homologous recombination method from the strain into which the exogenous 1,3-PD synthesis pathway and/or exogenous D-LAC synthesis pathway are introduced.

The method further provides a method for screening the bacterium, comprising the following operations: adding a soil sample into a first liquid culture medium for culture, and then transferring to a solid culture medium; inoculating a single colony grown on the solid culture medium into a second liquid culture medium for culture; and after culture, detecting yields of 1,3-propanediol and D-lactic acid in the second liquid culture medium, and picking out strains with the yields of 1,3-propanediol and D-lactic acid which satisfy requirements.

Further, the first liquid culture medium and the second liquid culture medium are glycerol liquid culture mediums; and the solid culture medium is a glycerol solid culture medium.

Further, the single colony refers to a single colony with acid-producing transparent circles.

The present invention further relates to application of the bacterium to production of 1,3-propanediol or D-lactic acid or coproduction of 1,3-propanediol and D-lactic acid.

The present invention further particularly relates to application of *Klebsiella oxytoca* PDL-5 CCTCC M 2016185 to production of 1,3-propanediol or D-lactic acid or coproduction of 1,3-propanediol and D-lactic acid.

The present invention provides a method for coproducing 1,3-propanediol and D-lactic acid by fermenting the bacterium. The method for coproducing 1,3-propanediol and D-lactic acid by fermenting the bacterium actually refers to the application of the bacterium.

Further, the method for coproducing 1,3-propanediol and D-lactic acid is characterized in that the bacterium is *Klebsiella oxytoca* PDL-5 CCTCC M 2016185.

Further, aeration speed during fermentation is 0-2.0 vvm. Preferably, aeration speed during fermentation is 0-1.0 vvm.

Further, mixed emulsion of calcium hydroxide and water is used as a neutralizer for regulating pH of fermentation solution during fermentation.

Further, the method for coproducing 1,3-propanediol and D-lactic acid comprises the following steps:

step (1): strain selection: selecting *Klebsiella oxytoca* PDL-5 CCTCC M 2016185;

step (2): seed culture; and step (3): fermentation: in a fermentation process, using a neutralizer for regulating pH of fermentation solution to 5.5-7.5.

Further, the method for coproducing 1,3-propanediol and D-lactic acid comprises the following steps:

step (1): strain selection: selecting *Klebsiella oxytoca* PDL-5 CCTCC M 2016185;

step (2): seed culture: selecting the strain in the step (1), inoculating into a glycerol culture medium under an aseptic condition and culturing for 6-24 h at 25-40° C. and shaker speed of 100-300 rpm to obtain seed culture solution; and step (3): fermentation: inoculating the seed culture solution obtained in the step (2) into a fermentation tank containing a glycerol culture medium, an inoculation amount v/v being 0.5-10%, fermentation temperature being 25-40° C., aeration speed being 0.3-2.0 vvm and stirring speed being 50-400 rpm, using a neutralizer for regulating pH of fermentation solution to 5.5-7.5 during fermentation, fermentation modes being batch fermentation or fed-batch fermentation, and when batch fermentation is performed and glycerol in the glycerol culture medium is used up, stopping fermentation; and when fed-batch fermentation is performed and glycerol in the glycerol culture medium is used up, controlling the concentration of glycerol in the fermentation solution to be 5-40 g/L by supplementing 400-800 g/L glycerol solution into the fermentation tank, and stopping fermentation when the concentration of 1,3-propanediol or D-lactic acid in the fermentation solution does not increase.

Further, in the step (2), the fermentation temperature is 30-37° C., the shaker speed is 150-250 rpm and the culture time is 10-16 h; in the step (3), the inoculation amount v/v is 2-6%, the fermentation temperature is 30-37° C., the aeration speed is 0.7-1.5 vvm, the stirring speed is 150-300 rpm, pH of the fermentation solution is regulated to 6.0-7.0, the fermentation mode is fed-batch fermentation, the concentration of glycerol in the supplemented glycerol solution is 500-700 g/L and the concentration of glycerol in the fermentation solution is controlled to be 10-30 g/L; and in the step (3), the neutralizer comprises any one or more of sodium hydroxide aqueous solution, potassium hydroxide aqueous solution, ammonia aqueous solution and mixed emulsion of calcium hydroxide and water.

The present invention has the following beneficial effects:

1. By using *Klebsiella oxytoca* PDL-5 CCTCC M 2016185, the concentration of target products in the obtained fermentation solution is high, the types of byproducts are few and the concentration of byproducts is low. 1,3-PD with concentration exceeding 70 g/L and D-LAC with concentration exceeding 110 g/L can be produced, the total conversion rate of 1,3-PD and D-LAC exceeds 90%, and the produced D-LAC has high optical purity (purity greater than 99.9%). Only a small amount of byproducts acetic acid (2.3 g/L) and succinic acid (4.1 g/L) can be detected in the fermentation solution.

Coproduction of 1,3-PD and optically pure LAC (L-LAC and D-LAC) has the following advantages: since the way that *Klebsiella oxytoca* metabolizes glycerol is a glycerol disproportionation pathway, which is divided into a glycerol oxidization pathway and a glycerol reduction pathway. Conversion from glycerol to 1,3-PD is a glycerol reduction pathway, and cofactors NADH and ATP produced in the oxidization pathway are needed to provide reducing power and energy in the conversion process. Lactic acid was selected as one of first thirty platform compounds to be greatly developed by the United States Department of Energy in 2004. In view of its wide use, it was further selected as one of the most promising platform compounds in 2010. Lactic acid is an important monomer and can be used for synthesizing a biodegradable, biocompatible and environmental-friendly biological polymer polylactic acid (PLA). By adding an isomeride D-lactic acid into PLA, the performance of PLA can be obviously improved and the application thereof to polymer materials is facilitated; in addition to the economic value of lactic acid, 1 mol of net NADH is produced in the process of lactic acid synthesis and can provide reducing power for synthesizing 1,3-PD, so as to achieve a balanced state of reducing power; in the process of conversion from glycerol to lactic acid, the conversion is conversion from C3 to C3, there is no carbon loss and the recovery rate of carbon can be guaranteed; in addition, lactic acid has a very good biocompatibility and this is critical to high-yield production of lactic acid in the industry; and since biological synthesis of lactic acid has already realized industrial-level production, the downstream purification technology is relatively mature. All of these features enable lactic acid to become an optimum choice for coproduction with 1,3-PD. As proved by facts, through coproduction of 1,3-PD and D-LAC, a very high total conversion rate (exceeding 90%) is achieved. According to the current reports (Biotechnol Bioeng. Metabolism in 1,3-propanediol fed-batch fermentation by a D-lactate deficient mutant of *Klebsiella pneumoniae*. 2009; 104(5):965-72; Bioresour Technol. Production of optically pure d-lactate from glycerol by engineered *Klebsiella pneumoniae* strain. 2014; 172:269-75), in *Klebsiella oxytoca*, the highest yield of 1,3-PD synthesized through direct conversion from glycerol is 95.4 g/L, and the molar conversion rate from glycerol to 1,3-PD is 0.48 mol/mol (i.e., 48%); and the highest yield of D-lactic acid obtained through direct conversion from glycerol is 142.1 g/L and the conversion rate is 0.84 mol/mol (84%). However, according to the current reports, there is no strain capable of simultaneously producing 1,3-PD and optically pure LAC (L-LAC or D-LAC).

Since in industrial large-scale production, factors such as product concentration, conversion rate and extraction cost must be considered, if simultaneous production of 1,3-PD and optically pure LAC (L-LAC and D-LAC) at high molar conversion rate by using one strain can be realized by using glycerol as a substrate and taking 1,3-PD and optically pure LAC (L-LAC and D-LAC) as main products, the production cost will be greatly reduced and the production efficiency will be improved.

2. *Klebsiella oxytoca* PDL-5 CCTCC M 2016185 can be easily centrifuged and filtered, and thus the high-efficiency biological process production and extraction of biological material monomers 1,3-PD and D-LAC are facilitated.

3. *Klebsiella oxytoca* PDL-5 CCTCC M 2016185 has an important practical application value.

4. By using calcium hydroxide as a fermentation neutralizer for regulating pH, the improvement of the yields of 1,3-PD and D-LAC in the fermentation solution is facilitated. As shown by fed-batch data, the yields of 1,3-PD and D-LAC are respectively 74.5 g/L and 111.9 g/L, the cell OD reaches 12.5, and the values are respectively improved by 81.2%, 56.5% and 135.8% as compared with NaOH when being used as a neutralizer.

5. Concentration of 1,3-PD and D-LAC coproduced by *Klebsiella oxytoca* PDL-0, PDL-1, PDL-2, PDL-3, PDL-4 and PDL-5 is not greatly different, and the mass ratio is within 1:0.1-10, especially within 1:0.2-5, and further within 1:0.5-2.

DETAILED DESCRIPTION OF THE PREFERRED EMBODIMENTS

The technical content of the present invention will be further described below in combination with the embodiments. The following embodiments are descriptive rather than restrictive, and the protective scope of the present invention shall not be defined by the following embodiments. Unless otherwise specially stated, experimental methods used in the following embodiments are all conventional methods. Unless otherwise specially stated, materials, reagents and the like used in the following embodiments can be commercially obtained.

Figure 1:
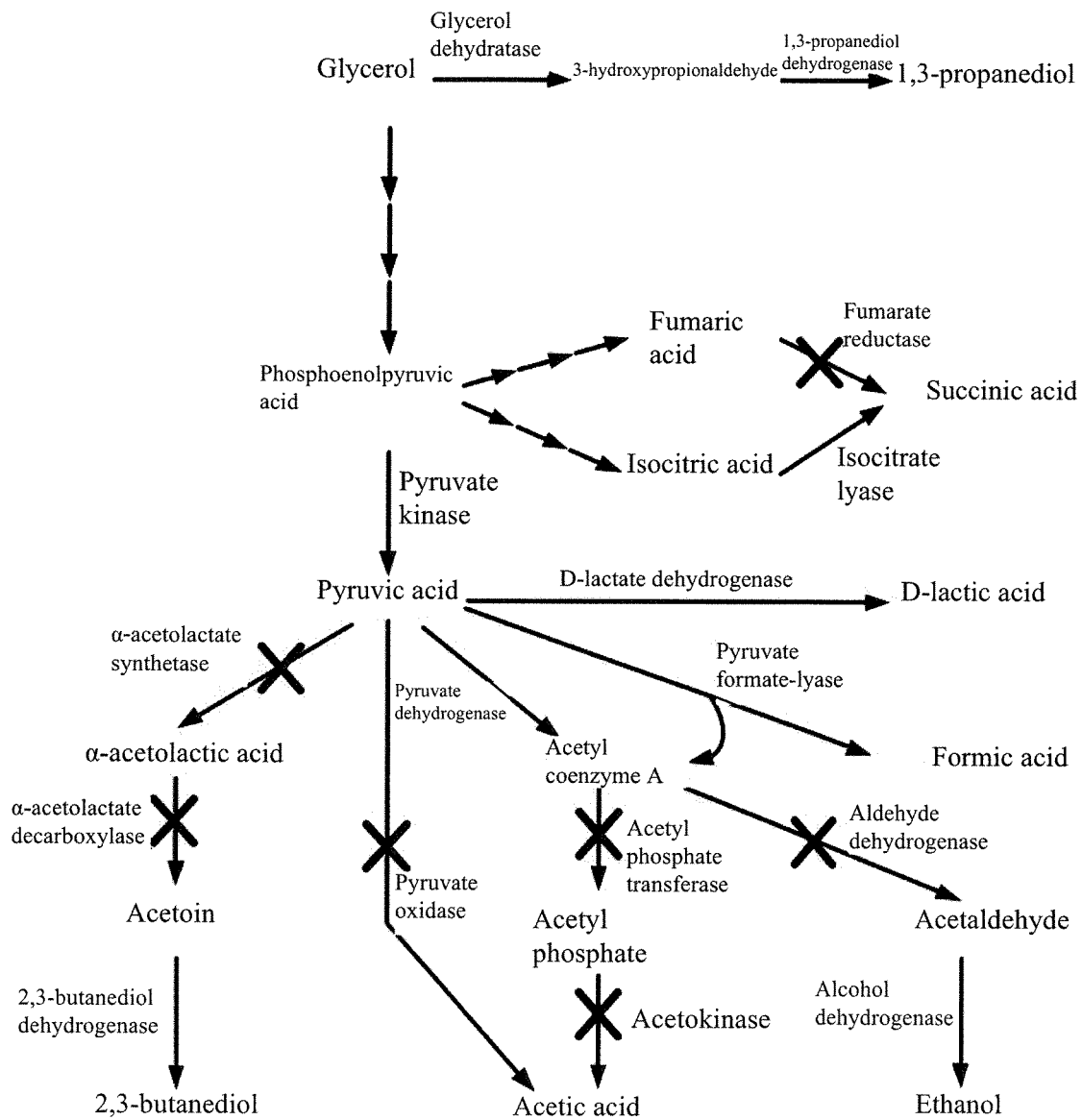
FIG. 1 is a schematic diagram of gene modification performed to *Klebsiella oxytoca*.

In the *Klebsiella oxytoca* PDL-5 CCTCC M 2016185 provided by the present invention, since budA, budB, adhE, ackA-pta, poxB and frdA genes are defected, activities of α-acetolactate decarboxylase, α-acetolactate synthetase, aldehyde dehydrogenase, acetokinase, acetyl phosphate transferase, pyruvate oxidase and fumarate reductase are caused to be lost, and 2,3-butanediol, ethanol, acetic acid and succinic acid metabolic pathways are deactivated, as illustrated in FIG. 1. From FIG. 1, it can be seen that glycerol can be converted to obtain 1,3-propanediol and D-lactic acid, and the following metabolic pathways are deactivated: pathway for α-acetolactate synthetase to catalyze pyruvic acid to produce α-acetolactic acid; pathway for α-acetolactate decarboxylase to catalyze α-acetolactic acid to produce acetoin; pathway for pyruvate oxidase to catalyze pyruvic acid to produce acetic acid; pathway for acetyl phosphate transferase to catalyze acetyl coenzyme A to produce acetyl phosphate; pathway for acetokinase to catalyze acetyl phosphate to produce acetic acid; pathway for aldehyde dehydrogenase to catalyze acetyl coenzyme A to produce acetaldehyde; and pathway for fumarate reductase to catalyze fumaric acid to produce succinic acid. In FIG. 1, X mark expresses that the activity of the enzyme is lost and the corresponding metabolic pathway is deactivated.

By using *Klebsiella oxytoca* PDL-5 CCTCC M 2016185 and using glycerol as a substrate, high-concentration 1,3-PD and high-concentration D-LAC can be produced. No L-LAC is detected in the fermentation solution and thus the produced D-LAC has high optical purity (purity greater than 99.9%). No 2,3-butanediol, ethanol and formic acid are detected in the fermentation solution, only a small amount of acetic acid and succinic acid can be detected, and detection results of products in the fermentation solution are as shown in Table 1.

TABLE 1

Product components in fermentation solution of *Klebsiella oxytoca* PDL-5 CCTCC M 2016185 using glycerol as substrate

| Product | Concentration (g/L) | Molar conversion rate (%) |
|---|---|---|
| 1,3-PD | 76.2 | 42.6 |
| D-LAC | 111.9 | 52.8 |
| L-LAC | 0 | 0 |
| 2,3-butanediol | 0 | 0 |
| Ethanol | 0 | 0 |
| Acetic acid | 2.3 | 1.6 |
| Succinic acid | 4.1 | 1.5 |
| Formic acid | 0 | 0 |

As shown in Table 1, *Klebsiella oxytoca* PDL-5 CCTCC M 2016185, by using glycerol as a substrate, can produce 76.2 g/L 1,3-PD and 111.9 g/L D-LAC, wherein the molar conversion rate of 1,3-PD reaches 42.6%, the molar conversion rate of D-LAC reaches 52.8%, and the total conversion rate of two main products 1,3-PD and D-LAC exceeds 90%. Only a small amount of byproducts acetic acid and succinic acid can be detected in the fermentation solution.

Embodiment 1: Screening and Identification of Strain Taking 1,3-PD and LAC as Main Products 2 g of soil sample was weighed and added into a 50 ml of glycerol liquid culture medium, the mixture was placed in a shaker for culture for 24 h at 37° C., and the shaker speed is 200 rpm. Then, aseptic normal saline was used for diluting the culture liquid respectively by 10 times, 100 times, 1000 times and 10000 times, then the culture liquid was coated into culture dishes containing a glycerol solid culture medium, and static culture was performed for 24 h at 37° C. After single colonies grew, single colonies with large colony area and acid-producing transparent circles were selected and inoculated into glycerol liquid culture mediums, the mixture was placed in a shaker for culture for 24 h at 37° C., and the shaker speed was 200 rpm. Centrifugation was performed to the culture solution, the yields of 1,3-PD and LAC in the culture solution were determined, and a strain which highly produces 1,3-PD and LAC and is easily centrifugated was picked.

The strain was purified repetitively through streaking on the glycerol solid culture medium, then 10 cycles of culture testing were performed, the yields and molar conversion rates of 1,3-PD and LAC produced in the 10 cycles of culture were substantially kept at original levels, and thus it indicated that the strain is the target strain, which was named as PDL-0. The proportions of D-LAC and L-LAC in the strain PDL-0 culture medium were determined. As shown by results, in LAC produced by the strain PDL-0, the proportion of D-LAC was greater than 99.9% and the proportion of L-LAC was smaller than 0.01%.

A whole genome of the strain PDL-0 was extracted, then a gene sequence of 16S rRNA of the strain PDL-0 was amplified through PCR amplification, a PCR product was sequenced, and a 16S rRNA gene sequence obtained through sequencing was as expressed by SEQ ID NO:7. The 16S rRNA gene sequence of the strain PDL-0 had 99% of homology with the 16S rRNA gene sequence of other *Klebsiella oxytoca* in NCBI database (http://www.ncbi.nlm-.nih.gov/), and as shown by analysis results, the strain PDL-0 was *Klebsiella oxytoca*.

Herein, a formula of the glycerol liquid culture medium was as follows: 3 g/L yeast powder, 10 g/L $K_2HPO_4.3H_2O$, 2 g/L $KH_2PO_4$, 1 g/L $NH_4Cl$, 0.5 g/L $MgSO_4.7H_2O$, 20 mg/L $FeCl_3.6H_2O$, 50 mg/L $CoCl_2.6H_2O$ and 20 g/L glycerol; and sterilization was performed for 20 min at 121° C.

Herein, a formula of the glycerol solid culture medium was as follows: 3 g/L yeast powder, 10 g/L $K_2HPO_4.3H_2O$, 2 g/L $KH_2PO_4$, 1 g/L $NH_4Cl$, 0.5 g/L $MgSO_4.7H_2O$, 20 mg/L $FeCl_3.6H_2O$, 50 mg/L $CoCl_2.6H_2O$, 20 g/L glycerol and 15 g/L agar powder; and sterilization was performed for 20 min at 121° C.

Embodiment 1 gives a method for screening a strain coproducing 1,3-PD and D-LAC, wherein the involved numerical value ranges shall not be understood as limitations to the present invention, and the similar effects can also be achieved through variations within reasonable ranges. The strain obtained by adopting the screening method is not limited to PDL-0, and may be a strain of other species or another different stain of the same species.

Embodiment 2: Defecting of α-Acetolactate Decarboxylase Gene (budA) and α-Acetolactate Synthetase Gene (budB) in *Klebsiella oxytoca* PDL-0

(1) Construction of Vector for Partially Deleted budA Gene in *Klebsiella oxytoca* PDL-0

Primers were designed according to a budA gene sequence (as expressed by SEQ ID NO:1), and upstream and downstream homologous segments of the budA gene were amplified through PCR amplification. A genome DNA of *Klebsiella oxytoca* PDL-0 was used as a template, and PCR amplification was performed by using a primer budA-1 5'-ACATGATTACGAATTCATGAACCATTCTGCT-GAATG-3' (as expressed by SEQ ID NO:8) and a primer budA-2 5'-AACGGGCTGGCAT-CACCGCGAAGGGCGTGC-3' (as expressed by SEQ ID NO:9) to obtain an upstream homologous segment; PCR amplification was performed by using a primer budA-3 5'-CGCGGTGATGCCAGCCCGTTTTCCGCTTCA-3' (as expressed by SEQ ID NO:10) and a primer budA-4 5'-TACCGAGCTCGAATTCTTAGTTTTCGACT-GAGCGAA-3' (as expressed by SEQ ID NO:11) to obtain a downstream homologous segment. PCR amplification conditions were as follows: 5 min at 95° C.; 30 sec at 95° C., 30 sec at 60° C., 1 min at 72° C., and totally 30 cycles; and 5 min at 72° C. After PCR reaction was ended, 1.0% agarose gel electrophoresis was performed to PCR amplification products, and recovery and purification were performed to obtain upstream and downstream homologous segments.

Enzyme digestion was performed to a suicide plasmid pKR6K by using restriction endonuclease EcoRI (Wang et al., J. Biol. Chem. 2014, 289:6080-6090), 1.0% agarose gel electrophoresis was performed to enzyme digestion products, and recovery and purification were performed to obtain a linearized plasmid pKR6K. The suicide plasmid pKR6K may be obtained by replacing a replicon of a plasmid pK18mobsacB (YouBio Company) with a replicon of a plasmid pCAM140. A sequence of the replicon of the plasmid pCAM140 may be obtained by means of gene synthesis, and for a sequence of the plasmid pCAM140, see the literature report Wilson K J, Sessitsch A, Corbo J C, et al. β-Glucuronidase (GUS) transposons for ecological and genetic studies of *rhizobia* and other Gram-negative bacteria [J]. Microbiology, 1995, 141(7): 1691-1705).

The upstream homologous segment, the downstream homologous segment and the linearized plasmid pKR6K were linked by using a seamless cloning and assembly kit (pEASY-Uni Seamless Cloning and Assembly Kit manufactured by Beijing TransGen Biotech Co., Ltd.) to obtain a suicide plasmid pKR6K-ΔbudA with a budA gene which can be partially deleted.

(2) Construction of *Klebsiella oxytoca* with Partially Deleted budA Gene pKR6K-ΔbudA was transformed into *Escherichia coli* S17-1(λpir) (Beijing TransGen Biotech Co., Ltd.) to obtain donor *Escherichia coli* S17-1(λpir) (pKR6K-ΔbudA). Biparental hybridization was performed to the donor *Escherichia coli* S17-1(λpir) (pKR6K-ΔbudA) and receptor *Klebsiella oxytoca* PDL-0 to enable budA gene upstream homologous segment and downstream homologous segment on pKR6K-ΔbudA and a genome of *Klebsiella oxytoca* PDL-0 to experience homologous recombination, so as to enable the budA gene of *Klebsiella oxytoca* PDL-0 to be deleted for 200 bp to achieve the purpose of enabling the budA gene to be defected. A specific method was as follows:

a. A donor and a receptor which were activated were respectively inoculated into 5 mL of LB liquid culture medium, culture was performed for 2-3 h at 37° C. in a shaker at shaking speed of 200 rpm, when the donor and receptor simultaneously grew to $OD_{620\ nm}$ of 0.5-0.8, centrifugation was performed to 5 mL of donor solution, and washing was performed twice by using aseptic normal saline; centrifugation was performed to 1 mL of receptor solution and washing was performed twice by using aspect normal saline; and thalli of the donor and receptor were resuspended totally by using 100 μL of aseptic normal saline, resuspended solution was fully dropped into a middle of an LB solid culture medium plate, and the plate was placed frontally and culture was performed for 12-18 h at 37° C.

b. A colony on the LB solid culture medium plate in step a was scraped down by using aseptic normal saline and a scraper, washing was performed twice by using aseptic normal saline, proper dilution was performed, the colony was coated onto an M9 solid culture medium plate added with 50 μg/mL kanamycin, and culture was performed for 24-36 h at 37° C.

c. A single colony grown on the M9 solid culture medium plate in step b was picked and placed into 5 mL of LB liquid culture medium added with 50 μg/mL kanamycin, and culture was performed for 12 h at 37° C. and 200 rpm. The bacteria solution was transferred into 5 mL of fresh LB liquid culture medium (added with no kanamycin), and culture was performed for 12 at 37° C. and 200 rpm.

d. Proper dilution was performed to the bacteria solution, and the bacteria solution was coated onto an LAS solid culture medium plate, culture was performed for 24 h at 25° C.

e. A single colony grown on the LAS solid culture medium plate in step d was picked and placed into 5 mL of LB liquid culture medium, culture was performed for 12 h at 37° C. and 200 rpm, genome DNA was extracted, and PCR verification was performed by using a primer budA-1 5'-ACATGATTACGAATTCATGAACCATTCTGCTGAATG-3' (as expressed by SEQ ID NO:8) and a primer budA-4 5'-TACCGAGCTCGAATTCTTAGTTTTCGACTGAGCGAA-3' (as expressed by SEQ ID NO:11). A strain with a defected budA gene was obtained.

Herein, a formula of the LB liquid culture medium was as follows: 10 g/L peptone, 5 g/L yeast powder and 10 g/L NaCl. Sterilization was performed for 20 min at 121° C.

Herein, a formula of the LB solid culture medium was as follows: 10 g/L peptone, 5 g/L yeast powder, 10 g/L NaCl and 15 g/L agar powder. Sterilization was performed for 20 min at 121° C.

Herein, a formula of the M9 solid culture medium was as follows: 1.7 g/L $Na_2HPO_4.12H_2O$, 0.3 g/L $KH_2PO_4$, 0.05 g/L NaCl, 0.1 g/L $NH_4Cl$, 0.5 g/L trisodium citrate and 15 g/L agar powder. Sterilization was performed for 20 min at 121° C.

Herein, a formula of the LAS solid culture medium was as follows: 10 g/L peptone, 150 g/L sucrose and 15 g/L agar powder. Sterilization was performed for 20 min at 115° C.

(3) Construction of Vector for Partially Deleted budB Gene in Strain with Defected budA Gene Primers were designed according to a budB gene sequence (as expressed by SEQ ID NO:2), and upstream and downstream homologous segments of the budB gene were amplified through PCR amplification. A genome DNA of *Klebsiella oxytoca* PDL-0 was used as a template, and PCR amplification was performed by using a primer budB-1 5'-ACGCGAATTCGTGGATAATCAACATCAACCGCGCC-3' (as expressed by SEQ ID NO:12) and a primer budB-2 5'-ACGCGGATCCGGGGCGTCCCTGCTCGGC-3' (as expressed by SEQ ID NO:12) to obtain an upstream homologous segment; PCR amplification was performed by using a primer budB-3 5'-ACGCGGATCCATCGCCCGCTATCTCTACAGCTTCC-3' (as expressed by SEQ ID NO:14) and a primer budB-4 5'-ACGCCTGCAGATTTGACTGAGATGAAGCTGGCCCA-3' (as expressed by SEQ ID NO:15) to obtain a downstream homologous segment. PCR amplification conditions were as follows: 5 min at 95° C.; 30 sec at 95° C., 30 sec at 60° C., 1 min at 72° C., and totally 30 cycles; and 5 min at 72° C. After PCR reaction was ended, 1.0% agarose gel electrophoresis was performed to PCR amplification products, and recovery and purification were performed to obtain upstream and downstream homologous segments.

Enzyme digestion was performed to an upstream homologous segment by using restriction endonuclease EcoRI and BamHI, enzyme digestion was performed to a downstream homologous segment by using restriction endonuclease BamHI and PstI, enzyme digestion was performed to a suicide plasmid pKR6K by using restriction endonuclease EcoRI and PstI (Wang et al., J. Biol. Chem. 2014, 289:6080-6090), 1.0% agarose gel electrophoresis was performed to enzyme digestion products, and recovery and purification were performed to obtain a linearized plasmid pKR6K and upstream and downstream homologous segments with sticky ends.

The upstream homologous segment and the downstream homologous segment with sticky ends and the linearized plasmid pKR6K were linked by using a T4 ligase (NEB Company) to obtain a suicide plasmid pKR6K-ΔbudB with a budB gene which can be partially deleted.

(4) Construction of *Klebsiella oxytoca* with Partially Deleted budB Gene pKR6K-ΔbudB was transformed into *Escherichia coli* S17-1(λpir) to obtain donor *Escherichia coli* S17-1(λpir) (pKR6K-ΔbudB). Biparental hybridization was performed to the donor *Escherichia coli* S17-1(λpir) (pKR6K-ΔbudB) and a strain with a defected receptor budA gene to enable budB gene upstream homologous segment and downstream homologous segment on pKR6K-ΔbudB and a genome of strain with the defected receptor budA gene to experience homologous recombination, so as to enable the budB gene of the strain with the defected receptor budA gene to be deleted for 722 bp to achieve the purpose of enabling the budB gene to be defected. A specific method was the same as that in step (2), and a difference only lied in that, during PCR verification, the primer budB-1 5'-ACGCGAAT-TCGTGGATAATCAACATCAACCGCGCC-3' (as expressed by SEQ ID NO:12) and the primer budB-4 5'-ACGCCTGCAGATTTGACTGAGAT-GAAGCTGGCCCA-3' (as expressed by SEQ ID NO:15) were used. The obtained strain with the defected budA gene and budB gene was named as *Klebsiella oxytoca* PDL-1.

Embodiment 3: Defecting of Aldehyde Dehydrogenase Gene (adhE) in *Klebsiella oxytoca* PDL-1

(1) Construction of Vector for Partially Deleted adhE Gene in *Klebsiella oxytoca* PDL-1

Primers were designed according to an adhE gene sequence (as expressed by SEQ ID NO:3), and upstream and downstream homologous segments of the adhE gene were amplified through PCR amplification. A genome DNA of *Klebsiella oxytoca* PDL-1 was used as a template, and PCR amplification was performed by using a primer adhE-1 5udA-1s a template, and PCR amplification (as expressed by SEQ ID NO:16) and a primer adhE-2 5'-TGCTGTCTGTTGGCGTTACGGGTCTTCAGG-3' (as expressed by SEQ ID NO:17) to obtain an upstream homologous segment; PCR amplification was performed by using a primer adhE-3 5'-CGTAACGCCAACAGACAG-CATTCAGCCAGT-3' (as expressed by SEQ ID NO:18) and a primer adhE-4 5'-TACCGAGCTCGAATTCTTAAGCG-GATTTTTTCGCTT-3' (as expressed by SEQ ID NO:19) to obtain a downstream homologous segment. PCR amplification conditions were as follows: 5 min at 95° C.; 30 sec at 95° C., 30 sec at 60° C., 1 min at 72° C., and totally 30 cycles; and 5 min at 72° C. After PCR reaction was ended, 1.0% agarose gel electrophoresis was performed to PCR amplification products, and recovery and purification were performed to obtain upstream and downstream homologous segments.

Enzyme digestion was performed to a suicide plasmid pKR6K by using restriction endonuclease EcoRI (Wang et al., J. Biol. Chem. 2014, 289:6080-6090), 1.0% agarose gel electrophoresis was performed to enzyme digestion products, and recovery and purification were performed to obtain a linearized plasmid pKR6K.

The upstream homologous segment, the downstream homologous segment and the linearized plasmid pKR6K were linked by using a seamless cloning and assembly kit (pEASY-Uni Seamless Cloning and Assembly Kit manufactured by Beijing TransGen Biotech Co., Ltd.) to obtain a suicide plasmid pKR6K-ΔadhE with an adhE gene which can be partially deleted.

(2) Construction of *Klebsiella oxytoca* with Partially Deleted adhE Gene pKR6K-ΔadhE was transformed into *Escherichia coli* S17-1(λpir) to obtain donor *Escherichia coli* S17-1(λpir) (pKR6K-ΔadhE). Biparental hybridization was performed to the donor *Escherichia coli* S17-1(λpir) (pKR6K-ΔadhE) and receptor *Klebsiella oxytoca* PDL-1 to enable adhE gene upstream homologous segment and downstream homologous segment on pKR6K-ΔadhE and a genome of *Klebsiella oxytoca* PDL-1 to experience homologous recombination, so as to enable the adhE gene of *Klebsiella oxytoca* PDL-1 to be deleted for 1876 bp to achieve the purpose of enabling the adhE gene to be defected. A specific method was the same as that in embodiment 2, and a difference only lied in that, during PCR verification, the primer adhE-1 5'-ACATGAT-TACGAATTCATGGCTGTTACTAATGTCGC-3' (as expressed by SEQ ID NO:16) and the primer adhE-4 5'-TACCGAGCTCGAATTCTTAAGCGGAT-TTTTTCGCTT-3' (as expressed by SEQ ID NO:19). The obtained strain with the defected adhE gene was named as *Klebsiella oxytoca* PDL-2.

Embodiment 4: Defecting of Acetokinase and Acetyl Phosphate Transferase Gene (ackA-pta) in *Klebsiella oxytoca* PDL-2

(1) Construction of Vector for Partially Deleted ackA-pta Gene in *Klebsiella oxytoca* PDL-2

Primers were designed according to an ackA-pta gene sequence (as expressed by SEQ ID NO:4), and upstream and downstream homologous segments of the ackA-pta gene were amplified through PCR amplification. A genome DNA of *Klebsiella oxytoca* PDL-2 was used as a template, and PCR amplification was performed by using a primer ackA-pta-1 5'-ACATGATTACGAATTCATGTCGAGTAAGT-TAGTACT-3' (as expressed by SEQ ID NO:20) and a primer ackA-pta-2 5'-CACGCGCGGTCCTCAGCGATACC-GATCAGG-3' (as expressed by SEQ ID NO:21) to obtain an upstream homologous segment; PCR amplification was performed by using a primer ackA-pta-3 5'-ATCGCT-GAGGACCGCGCGTGGCCATGCTCT-3' (as expressed by SEQ ID NO:22) and a primer ackA-pta-4 5'-TACCGAGCTCGAATTCT-TATGCTTGCTGCTGGGACG-3' (as expressed by SEQ ID NO:23) to obtain a downstream homologous segment. PCR amplification conditions were as follows: 5 min at 95° C.; 30 sec at 95° C., 30 sec at 60° C., 1 min at 72° C., and totally 30 cycles; and 5 min at 72° C. After PCR reaction was ended, 1.0% agarose gel electrophoresis was performed to PCR amplification products, and recovery and purification were performed to obtain upstream and downstream homologous segments.

Enzyme digestion was performed to a suicide plasmid pKR6K by using restriction endonuclease EcoRI (Wang et al., J. Biol. Chem. 2014, 289:6080-6090), 1.0% agarose gel electrophoresis was performed to enzyme digestion products, and recovery and purification were performed to obtain a linearized plasmid pKR6K.

The upstream homologous segment, the downstream homologous segment and the linearized plasmid pKR6K were linked by using a seamless cloning and assembly kit (pEASY-Uni Seamless Cloning and Assembly Kit manufactured by Beijing TransGen Biotech Co., Ltd.) to obtain a suicide plasmid pKR6K-ΔackA-pta with an ackA-pta gene which can be partially deleted.

(2) Construction of *Klebsiella oxytoca* with Partially Deleted ackA-pta Gene pKR6K-ΔackA-pta was transformed into *Escherichia coli* S17-1(λpir) to obtain donor *Escherichia coli* S17-1(λpir) (pKR6K-ΔackA-pta). Biparental hybridization was performed to the donor *Escherichia coli* S17-1(λpir) (pKR6K-ΔackA-pta) and receptor *Klebsiella oxytoca* PDL-2 to enable ackA-pta gene upstream homologous segment and downstream homologous segment on pKR6K-ΔackA-pta and a genome of *Klebsiella oxytoca* PDL-2 to experience homologous recombination, so as to enable the ackA-pta gene of *Klebsiella oxytoca* PDL-2 to be deleted for 2749 bp to achieve the purpose of enabling the ackA-pta gene to be defected. A specific method was the same as that in embodiment 2, and a difference only lied in that, during PCR verification, the primer ackA-pta-1 5'-ACATGAT- TACGAATTCATGTCGAGTAAGTTAGTACT-3' (as expressed by SEQ ID NO:20) and the primer ackA-pta-4 5'-TACCGAGCTCGAATTCT-TATGCTTGCTGCTGGGACG-3' (as expressed by SEQ ID NO:23). The obtained strain with the defected ackA-pta gene was named as *Klebsiella oxytoca* PDL-3.

Embodiment 5: Defecting of Pyruvate Oxidase Gene (poxB) in *Klebsiella oxytoca* PDL-3

(1) Construction of Vector for Partially Deleted poxB Gene in *Klebsiella oxytoca* PDL-3

Primers were designed according to an poxB gene sequence (as expressed by SEQ ID NO:5), and upstream and downstream homologous segments of the poxB gene were amplified through PCR amplification. A genome DNA of *Klebsiella oxytoca* PDL-3 was used as a template, and PCR amplification was performed by using a primer poxB-1 5'-ACATGATTACGAATTCATGAAACA-GACCGTGGCGGC-3' (as expressed by SEQ ID NO:24) and a primer poxB-2 5'-AAAATCCCCGGGGTTGA-GACCAGTTCACAG-3' (as expressed by SEQ ID NO:25) to obtain an upstream homologous segment; PCR amplification was performed by using a primer poxB-3 5'-GTCT-CAACCCGGGGGATTTTCTCTCGCTGG-3' (as expressed by SEQ ID NO:26) and a primer poxB-4 5'-TACCGAGCTCGAATTCTTACCTTAGCCAGT-TAGTTT-3' (as expressed by SEQ ID NO:27) to obtain a downstream homologous segment. PCR amplification conditions were as follows: 5 min at 95° C.; 30 sec at 95° C., 30 sec at 60° C., 1 min at 72° C., and totally 30 cycles; and 5 min at 72° C. After PCR reaction was ended, 1.0% agarose gel electrophoresis was performed to PCR amplification products, and recovery and purification were performed to obtain upstream and downstream homologous segments.

Enzyme digestion was performed to a suicide plasmid pKR6K by using restriction endonuclease EcoRI (Wang et al., J. Biol. Chem. 2014, 289:6080-6090), 1.0% agarose gel electrophoresis was performed to enzyme digestion products, and recovery and purification were performed to obtain a linearized plasmid pKR6K.

The upstream homologous segment, the downstream homologous segment and the linearized plasmid pKR6K were linked by using a seamless cloning and assembly kit (pEASY-Uni Seamless Cloning and Assembly Kit manufactured by Beijing TransGen Biotech Co., Ltd.) to obtain a suicide plasmid pKR6K-ΔpoxB with a poxB gene which can be partially deleted.

(2) Construction of *Klebsiella oxytoca* with Partially Deleted poxB Gene pKR6K-ΔpoxB was transformed into *Escherichia coli* S17-1(λpir) to obtain donor *Escherichia coli* S17-1(λpir) (pKR6K-ΔpoxB). Biparental hybridization was performed to the donor *Escherichia coli* S17-1(λpir) (pKR6K-ΔpoxB) and receptor *Klebsiella oxytoca* PDL-3 to enable poxB gene upstream homologous segment and downstream homologous segment on pKR6K-ΔpoxB and a genome of *Klebsiella oxytoca* PDL-3 to experience homologous recombination, so as to enable the poxB gene of *Klebsiella oxytoca* PDL-3 to be deleted for 919 bp to achieve the purpose of enabling the poxB gene to be defected. A specific method was the same as that in embodiment 2, and a difference only lied in that, during PCR verification, the primer poxB-1 5'-ACATGAT-TACGAATTCATGAAACAGACCGTGGCGGC-3' (as expressed by SEQ ID NO:24) and the primer poxB-4 5'-TACCGAGCTCGAATTCTTACCTTAGCCAGT-TAGTTT-3' (as expressed by SEQ ID NO:27). The obtained strain with the defected poxB gene was named as *Klebsiella oxytoca* PDL-4.

Embodiment 6: Defecting of Fumarate Reductase Gene (frdA) in *Klebsiella oxytoca* PDL-1

(1) Construction of Vector for Partially Deleted frdA Gene in *Klebsiella oxytoca* PDL-4

Primers were designed according to a frdA gene sequence (as expressed by SEQ ID NO:6), and upstream and downstream homologous segments of the frdA gene were amplified through PCR amplification. A genome DNA of *Klebsiella oxytoca* PDL-4 was used as a template, and PCR amplification was performed by using a primer frdA-1 5'-ACATGATTACGAATTCGTGCAAACTTTT-CAAGCCGA-3' (as expressed by SEQ ID NO:28) and a primer frdA-2 5'-GTAGATGCCGAGCCGGTTT-TATCGGCAGCG-3' (as expressed by SEQ ID NO:29) to obtain an upstream homologous segment; PCR amplification was performed by using a primer frdA-3 5'-AAAACCGGCTCGGCATCTACCGTACGCCGG-3' (as expressed by SEQ ID NO:30) and a primer frdA-4 5'-TACCGAGCTCGAATTCTCAGCCAT-TCGTCGTCTCCT-3' (as expressed by SEQ ID NO:31) to obtain a downstream homologous segment. PCR amplification conditions were as follows: 5 min at 95° C.; 30 sec at 95° C., 30 sec at 60° C., 1 min at 72° C., and totally 30 cycles; and 5 min at 72° C. After PCR reaction was ended, 1.0% agarose gel electrophoresis was performed to PCR amplification products, and recovery and purification were performed to obtain upstream and downstream homologous segments.

Enzyme digestion was performed to a suicide plasmid pKR6K by using restriction endonuclease EcoRI (Wang et al., J. Biol. Chem. 2014, 289:6080-6090), 1.0% agarose gel electrophoresis was performed to enzyme digestion products, and recovery and purification were performed to obtain a linearized plasmid pKR6K.

The upstream homologous segment, the downstream homologous segment and the linearized plasmid pKR6K were linked by using a seamless cloning and assembly kit (pEASY-Uni Seamless Cloning and Assembly Kit manufactured by Beijing TransGen Biotech Co., Ltd.) to obtain a suicide plasmid pKR6K-ΔfrdA with a frdA gene which can be partially deleted.

(2) Construction of *Klebsiella oxytoca* with Partially Deleted frdA Gene pKR6K-ΔfrdA was transformed into *Escherichia coli* S17-1(λpir) to obtain donor *Escherichia coli* S17-1(λpir) (pKR6K-ΔfrdA). Biparental hybridization was performed to the donor *Escherichia coli* S17-1(λpir) (pKR6K-ΔfrdA) and receptor *Klebsiella oxytoca* PDL-4 to enable frdA gene upstream homologous segment and downstream homologous segment on pKR6K-ΔfrdA and a genome of *Klebsiella oxytoca* PDL-4 to experience homologous recombination, so as to enable the frdA gene of *Klebsiella oxytoca* PDL-4 to be deleted for 991 bp to achieve the purpose of enabling the frdA gene to be defected. A specific method was the same as that in embodiment 2, and a difference only lied in that, during PCR verification, the primer frdA-1 5'-ACATGAT-TACGAATTCGTGCAAACTTTTCAAGCCGA-3' (as expressed by SEQ ID NO:28) and the primer frdA-4 5'-TACCGAGCTCGAATTCTCAGCCAT-TCGTCGTCTCCT-3' (as expressed by SEQ ID NO:31). The obtained strain with the defected frdA gene was named as *Klebsiella oxytoca* PDL-5.

Embodiments 2-6 give methods for constructing strains with deactivated budA, budB, adhE, ackA-pta, poxB and frdA, i.e., gene defecting is realized by adopting a gene homologous recombination method to cause deactivation of enzymes coded thereby. However, methods causing deactivation of enzymes are not limited to gene homologous recombination, and may also be small RNA interference, point mutation, addition of inhibitors of related enzymes, etc.

Embodiment 7: Production of 1,3-PD and D-LAC by Using *Klebsiella oxytoca* PDL-5 CCTCC M 2016185 Through Batch Fermentation (1) Strain selection: *Klebsiella oxytoca* PDL-5 CCTCC M 2016185 was selected.

(2) Seed culture: the strain in the step (1) was selected and inoculated into a glycerol culture medium under an aseptic condition and culture was performed for 15 h at 30° C. and shaker speed of 200 rpm to obtain seed culture solution.

(3) Fermentation: the seed culture solution obtained in the step (2) was inoculated into a fermentation tank containing a glycerol culture medium, an inoculation amount was 5% (v/v), fermentation temperature was 35° C., aeration speed was 0.5 vvm and stirring speed was 200 rpm, 25% (w/v) sodium hydroxide aqueous solution was used as a neutralizer for regulating pH of fermentation solution to 7.0 during fermentation, the fermentation mode was batch fermentation, and when glycerol in the glycerol culture medium was used up, fermentation was stopped.

Herein, a formula of the glycerol culture medium was as follows: 2 g/L yeast powder, 5 g/L $K_2HPO_4.3H_2O$, 1 g/L $KH_2PO_4$, 2 g/L $NH_4Cl$, 0.1 g/L $MgSO_4.7H_2O$, 10 mg/L $FeCl_3.6H_2O$, 10 mg/L $CoCl_2.6H_2O$ and 60 g/L glycerol; and sterilization was performed for 20 min at 121° C.

After fermentation for 14 h, glycerol in the glycerol culture medium was used up, fermentation was stopped, and components and concentration of products in the fermentation solution were detected. Main fermentation products were 1,3-PD and D-LAC, the concentration of 1,3-PD was 23.1 g/L and the molar conversion rate was 46.6%; the concentration of D-LAC was 27.2 g/L and the molar conversion rate was 46.3%. For byproducts, only a small amount of acetic acid and succinic acid were detected, the concentration of acetic acid was 0.4 g/L and the molar conversion rate was 1.0%; and the concentration of succinic acid was 0.6 g/L and the molar conversion rate was 0.8%. No 2,3-butanediol, ethanol and formic acid were detected in the fermentation solution.

Embodiment 8: Production of 1,3-PD and D-LAC by Using *Klebsiella oxytoca* PDL-5 CCTCC M 2016185 Through Fed-Batch Fermentation (1) Strain selection: *Klebsiella oxytoca* PDL-5 CCTCC M 2016185 was selected.

(2) Seed culture: the strain in the step (1) was selected and inoculated into a glycerol culture medium under an aseptic condition and culture was performed for 12 h at 37° C. and shaker speed of 150 rpm to obtain seed culture solution.

(3) Fermentation: the seed culture solution obtained in the step (2) was inoculated into a fermentation tank containing a glycerol culture medium, an inoculation amount was 2.5% (v/v), fermentation temperature was 37° C., aeration speed was 1 vvm and stirring speed was 250 rpm, 25% (w/v) mixed emulsion of calcium hydroxide and water was used as a neutralizer for regulating pH of fermentation solution to 6.5 during fermentation, the fermentation mode was fed-batch fermentation, when glycerol in the glycerol culture medium was used up, the concentration of glycerol in the fermentation solution was controlled to be 5-30 g/L by supplementing 700 g/L glycerol solution into the fermentation tank, and when the concentration of 1,3-PD or D-LAC in the fermentation solution did not increase, fermentation was stopped.

Herein, a formula of the glycerol culture medium was as follows: 5 g/L yeast powder, 10 g/L $K_2HPO_4.3H_2O$, 2 g/L $KH_2PO_4$, 1 g/L $NH_4Cl$, 0.1 g/L $MgSO_4.7H_2O$, 20 mg/L $FeCl_3.6H_2O$, 15 mg/L $CoCl_2.6H_2O$ and 20 g/L glycerol; and sterilization was performed for 20 min at 121° C.

After fermentation for 30 h, the concentration of 1,3-PD and D-LAC in the fermentation solution did not increase, fermentation was stopped, and components and concentration of products in the fermentation solution were detected. Main fermentation products were 1,3-PD and D-LAC, the concentration of 1,3-PD was 76.2 g/L and the molar conversion rate was 42.6%; the concentration of D-LAC was 111.9 g/L and the molar conversion rate was 52.8%. For byproducts, only a small amount of acetic acid and succinic acid were detected, the concentration of acetic acid was 2.3 g/L and the molar conversion rate was 1.6%; and the concentration of succinic acid was 4.1 g/L and the molar conversion rate was 1.5%. No 2,3-butanediol, ethanol and formic acid were detected in the fermentation solution.

Embodiments 7 and 8 are just two preferred embodiments of the application method of the present invention, the numerical values defined therein, when vary in reasonable ranges, can also realize the same purpose, and thus the present invention is not limited by the numerical values given in embodiments 7 and 8. Although the fermentation products of *Klebsiella oxytoca* PDL-5 are detected in embodiments 7 and 8 and it provides that *Klebsiella oxytoca* PDL-5 can produce 1,3-PD and D-LAC at high molar conversion rates, it shall not be only understood as that the technical solution of gene modification of *Klebsiella oxytoca* disclosed by the present invention is only applicable to *Klebsiella oxytoca* PDL-5, and it shall be understood as that artificial bacteria as long as obtained by adopting the technical solution of gene modification of *Klebsiella oxytoca* disclosed by the present invention can have the abilities in improving the molar conversion rates of 1,3-PD and D-LAC and decreasing the byproducts. Besides, in embodiments 1-8, gene modification is performed by using *Klebsiella oxytoca* PDL-0 as a wild bacterium, and if the same gene modification is performed to other bacteria having the same metabolic pathways as *Klebsiella oxytoca* PDL-0, it shall be understood as that the molar conversion rates of 1,3-PD and D-LAC can be improved and the byproducts can be decreased as well at the same time.

By using *Klebsiella oxytoca* PDL-5 CCTCC M 2016185 and using glycerol as the substrate, after fed-batch fermentation, the concentration of target products 1,3-PD and D-LAC in the obtained fermentation solution is high, the types of byproducts are few and the concentration of byproducts is low. Besides, *Klebsiella oxytoca* PDL-5 CCTCC M 2016185 can be easily centrifuged and filtered, and thus these advantages facilitate the high-efficiency biological process production of 1,3-PD and D-LAC and simultaneously facilitate the extraction of the products, and it indicates that the *Klebsiella oxytoca* PDL-5 CCTCC M 2016185 provided by the present invention has an important practical application value.

Embodiment 9: Selection of Fermentation Neutralizer

A neutralizer NaOH commonly used in production of 1,3-PD is used a neutralizer for regulating pH, and after 30 h of fed-batch fermentation performed to the PDL-5 strain, the yield of 1,3-PD is 41.1 g/L and the yield of D-LAC 71.5 g/L. Optical density (OD) of cells at 620 nm can reach 5.3. Cell OD herein always refers to optical density of cells at 620 nm. After other commonly used neutralizers such as KOH and $NH_3H_2O$ are used, the yields of 1,3-PD and D-LAC do not obviously increase, and the yield of 1,3-PD is respectively 34.7 g/L and 34.8 g/L; the yield of D-LAC is respectively 61.6 g/L and 73.5 g/L; and cell OD is respectively 5.2 and 6.1.

Figure 2:
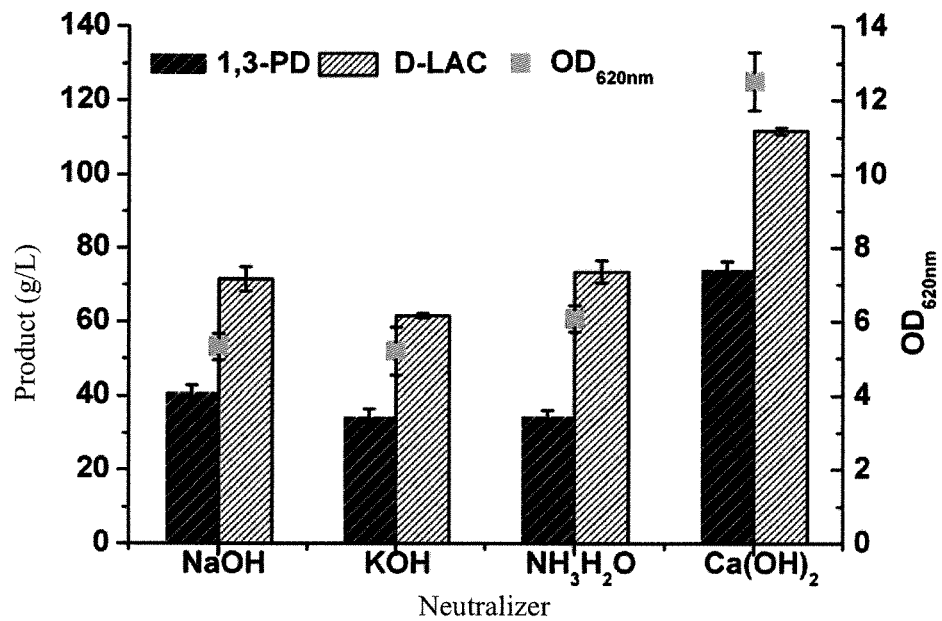
FIG. 2 is a histogram of influences of different neutralizers on fermentation products.

When $Ca(OH)_2$ is used as a neutralizer for coproduction of 1,3-PD and D-LAC, as shown by data of fed-batch fermentation of the PDL-5 strain for 30 h, the yields of 1,3-PD and D-LAC are respectively 76.2 g/L and 111.9 g/L, the cell OD reaches 12.5, and as compared with NaOH used as a neutralizer, the values are respectively improved by 85.4%, 56.5% and 135.8%, as illustrated in FIG. 2. Therefore, $Ca(OH)_2$ is selected as the final fermentation neutralizer.

It is analyzed that the reasons why the use of Ca(OH)2 as the fermentation neutralizer more greatly facilitates the coproduction of 1,3-PD and D-LAC are as follows: when common *Klebsiella oxytoca* metabolizes glycerol to synthesize 1,3-PD, main byproducts are generally organic alcohol such as 2,3-butanediol and ethanol, the amount of the synthesized acid is not great, and the production demand can be satisfied by using a small amount of neutralizers such as NaOH. However, the bacterium related to by the present invention synthesizes much lactic acid; and if NaOH or ammonia water is used for regulating pH, a great amount of sodium salt or amine salt will be produced, this two salts are easily dissociated, consequently cell osmotic pressure is too great and the growth and metabolism of cells are seriously inhibited. However, calcium lactate is not easily dissociated, the influence on cell osmotic pressure is small and thus cells can be allowed to synthesize lactic acid at a higher yield.

Embodiment 10: Optimization of Dissolved Oxygen Content in Fermentation Process Since a key enzyme glycerol dehydratase for synthesizing 1,3-PD is an oxygen-sensitive enzyme, if the dissolved oxygen content is too high, the synthesis of 1,3-PD will be inhibited. Therefore, fed air has an influence on the production thereof. It is also reflected in other reports about synthesis of 1,3-PD through metabolization of glycerol. Usually, the optimum fermentation condition of synthesis of 1,3-PD through fermentation of glycerol is microaerobic fermentation. However, in biological process synthesis of LAC, usually anaerobic fermentation is adopted. However, in the production process of synthesis of D-LAC through fermentation of glycerol by using *Klebsiella oxytoca* reported recently, the writer finds that, under a microaerobic fermentation condition, with the increase of the amount of fed air, the synthesis of D-LAC will increase. Therefore, in experiments of coproduction of two substances, the inventor also needs to pay great attention to the influence of dissolved oxygen content on carbon metabolic flux in cells. Therefore, the inventor adopts different aeration speed to achieve different dissolved oxygen contents, so as to observe and select the optimum condition to perform coproduction fermentation.

The inventor adopts anaerobic conditions and microaerobic contioins to perform coproduction fermentation in experiments. The specific implementation method is reflected by variation of aeration speed. The aeration speed is respectively 0, 0.5 vvm, 1.0 vvm and 2.0 vvm. Stirring speed is 250 rpm. Fermentation data are as shown in Table 2.

TABLE 2

Influence of aeration speed on fermentation product

| Aeration speed | 1,3-PD | Error bar | D-LAC | Error bar | $OD_{620nm}$ | Error bar |
|---|---|---|---|---|---|---|
| 0 vvm | 51.16 | 1.86 | 66.75 | 2.23 | 7.62 | 0.35 |
| 0.5 vvm | 57.11 | 0.54 | 106.91 | 1.36 | 11.46 | 0.45 |
| 1 vvm | 74.49 | 1.81 | 111.90 | 0.87 | 12.52 | 0.79 |
| 2 vvm | 50.99 | 2.12 | 116.72 | 0.50 | 12.96 | 0.64 |

Figure 3:
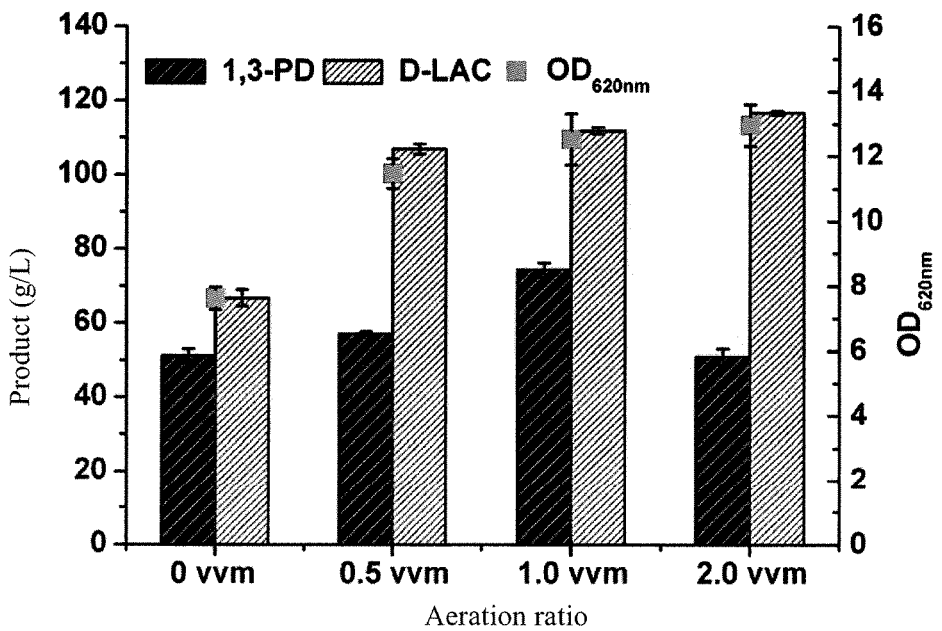
FIG. 3 is a histogram of influences of different aeration speed on fermentation products.

From data in Table 2 and FIG. 3 (a histogram drawn according to Table 2), a condition under which the highest yield of 1,3-PD can be realized is selected, i.e., the condition of aeration speed of 1.0 vvm is finally selected as the fed-batch condition.

Embodiment 11: Analysis on Production of 1,3-PD and D-LAC by *Klebsiella oxytoca* PDL-0

By using *Klebsiella oxytoca* PDL-0 and using glycerol as a substrate, fed-batch fermentation was performed, concentration of target products 1,3-PD and D-LAC in fermentation solution was high, and when 6M of NaOH was used as a fermentation neutralizer, the yields were respectively 35.0 g/L and 44.9 g/L, and the molar ratio was approximately 1:1. Byproducts were organic acid such as acetic acid, succinic acid and formic acid and organic alcohol such as 2,3-butanediol and ethanol. Concentration of each byproduct was relatively low. When wild PDL-0 was used and 25% (w/v) mixed emulsion of calcium hydroxide and water was used as a neutralizer for regulating pH of the fermentation solution, the final yields of 1,3-PD and D-LAC were respectively 50.7 g/L and 64.2 g/L, the molar conversion rates were respectively 36.5% and 39.0%, and the molar ratio was still approximately 1:1. The enzymatic characteristics of natural D-lactate dehydrogenase of this bacterium provide convenience for gene engineering modification of this bacterium.

Besides, this bacterium is easily centrifugated and filtered, these advantages facilitate the high-efficiency biological process production of 1,3-PD and D-LAC after gene engineering modification and simultaneously facilitate the extraction of the products, and it has an important practical application value.

Embodiment 12: Analysis on Production of 1,3-PD and D-LAC by *Klebsiella oxytoca* PDL-1

Fermentation Method:

(1) Strain selection: *Klebsiella oxytoca* PDL-1 was selected.

(2) Seed culture: the strain in the step (1) was selected and inoculated into a glycerol culture medium under an aseptic condition and culture was performed for 12 h at 37° C. and shaker speed of 150 rpm to obtain seed culture solution.

(3) Fermentation: the seed culture solution obtained in the step (2) was inoculated into a fermentation tank containing a glycerol culture medium, an inoculation amount was 2.5% (v/v), fermentation temperature was 37° C., aeration speed was 1 vvm and stirring speed was 250 rpm, 6M of sodium hydroxide was used as a neutralizer for regulating pH of fermentation solution to 6.5 during fermentation, the fermentation mode was fed-batch fermentation, when glycerol in the glycerol culture medium was used up, the concentration of glycerol in the fermentation solution was controlled to be 5-30 g/L by supplementing 700 g/L glycerol solution into the fermentation tank, and when the concentration of 1,3-PD or D-LAC in the fermentation solution did not increase, fermentation was stopped.

Herein, a formula of the glycerol culture medium was as follows: 5 g/L yeast powder, 10 g/L $K_2HPO_4 \cdot 3H_2O$, 2 g/L $KH_2PO_4$, 1 g/L $NH_4Cl$, 0.1 g/L $MgSO_4 \cdot 7H_2O$, 20 mg/L $FeCl_3 \cdot 6H_2O$, 15 mg/L $CoCl_2 \cdot 6H_2O$ and 20 g/L glycerol; and sterilization was performed for 20 min at 121° C.

After fermentation for 30 h, the concentration of 1,3-PD and D-LAC in the fermentation solution did not increase, fermentation was stopped, and components and concentration of products in the fermentation solution were detected.

Main fermentation products of PDL-1 were 1,3-PD and D-LAC, the concentration of 1,3-PD was 32.1 g/L and the concentration of D-LAC was 60.4 g/L. Byproducts ethanol, acetic acid, formic acid and succinic acid were detected, the concentration of ethanol was 1.7 g/L, the concentration of acetic acid was 0.9 g/L, the concentration of formic acid was 2.2 g/L and the concentration of succinic acid was 1.5 g/L. As compared with the wild type, no synthesized 2,3-butanediol was detected in the fermentation solution, the yield of D-LAC increased from 48.2 g/L to 60.1 g/L and the molar conversion rate increased from 39.1% to 52.7% relative to the wild type.

Embodiment 13: Analysis on Production of 1,3-PD and D-LAC by *Klebsiella oxytoca* PDL-2

The fermentation method was the same as the fermentation method in embodiment 12. However, the selected strain was *Klebsiella oxytoca* PDL-2. As shown by fermentation results, main products were 1,3-PD and D-LAC, the concentration of 1,3-PD was 43.5 g/L and the concentration of D-LAC was 59.3 g/L. Byproducts acetic acid, formic acid and succinic acid were detected, the concentration of acetic acid was 3.9 g/L, the concentration of formic acid was 1.1 g/L and the concentration of succinic acid was 1.5 g/L. As compared with PDL-1, no synthesized ethanol was detected in the fermentation solution, the yield of the D-LAC was substantially unchanged, the yield of 1,3-PD increased from 32.1 g/L to 43.5 g/L and the molar conversion rate increased from 33.2% to 40.0% relative to PDL-1.

Embodiment 14: Analysis on Production of 1,3-PD and D-LAC by *Klebsiella oxytoca* PDL-3

The fermentation method was the same as the fermentation method in embodiment 12. However, the selected strain was *Klebsiella oxytoca* PDL-3. As shown by fermentation results, main products were 1,3-PD and D-LAC, the concentration of 1,3-PD was 44.5 g/L and the concentration of D-LAC was 71.9 g/L. A small amount of byproducts acetic acid, formic acid and succinic acid were detected, the concentration of acetic acid was 1.5 g/L, the concentration of formic acid was 0.3 g/L and the concentration of succinic acid was 1.5 g/L. As compared with PDL-2, one pathway of acetic acid was knocked out to inhibit the synthesis of partial acetic acid, the yield of the 1,3-PD was substantially unchanged, the yield of, D-LAC increased from 59.3 g/L to 71.9 g/L and the molar conversion rate increased from 46.0% to 54.0%. After one pathway of acetic acid was knocked out, the molar conversion rate of acetic acid decreased from 4.5% to 1.6% relative to PDL-2.

Embodiment 15: Removal of Byproduct Formic Acid

Formic acid was a very important metabolic pathway for microbes in microaerobic and anaerobic fermentation. Catalyzed by pyruvate formate-lyase, pyruvic acid was cracked to produce formic acid and acetyl coenzyme A. Synthesized formic acid was detected in the wild type. Therefore, after a butanediol pathway and an ethanol pathway were knocked out, the inventor knocked out a gene pflB coding pyruvate formate-lyase. It was found that cell growth was obviously inhibited, cell OD decreased from 7.50 before knockout to 4.85 after knockout, and the yield of 1,3-PD also decreased from 43.4 g/L in the past to 37.9 g/L. This indicates the formic acid pathway is very important to cell metabolism, the knockout of this pathway will influence cell growth, and the reason is possibly that cells cannot provide enough acetyl coenzyme A inside to perform TCA cycles, and thus enough ATP cannot be provided for cell growth. On the basis of PDL-5 constructed in the present invention, the inventor knocked out the pflB gene, and found that, under a condition that Ca(OH)2 was used as a neutralizer, cell OD decreased from 12.5 in the past to 7.0, the yield of 1,3-PD decreased from 74.5 g/L to 40.5 g/L. Therefore, it further indicates the importance of the formic acid pathway to cell metabolism. This pathway shall not be deactivated.

Since formic acid can be metabolized by formate dehydrogenase and hydrogenase to produce $H_2$ and $CO_2$, as long as the fermentation condition is controlled to be a certain condition, formic acid synthesized in intermediary metabolism can be fully decomposed, and thus not only can the growth of thalli be prevented from being influenced, but also no formic acid is accumulated at last. This can be reflected in the fermentation process of PDL-5 in the process of engineering bacterium construction.

After the fermentation condition is optimized, a great amount of metabolic fluxes flow to 1,3-PD and LAC, a small amount of formic acid in the middle is fully metabolized after fermentation and thus a knockout strain PDL-5 which does not accumulate formic acid is obtained. It is also reflected in the strain PDL-4, and the finally accumulated formic acid is less than the formic acid accumulated by strains PDL-0 to PDL-3 in the metabolic process. Elimination of formic acid is a very complex process. It is very import to adjust the fermentation condition because different dissolved oxygen contents may cause enhancement or weakening of the pyruvic acid cracking pathway and thus increase or decrease the synthesis of formic acid.

Embodiment 16: Exogenous Introduction of New Pathway to Realize Coproduction of 1,3-PD and D-LAC

*Escherichia coli* K12 modified through gene engineering modification was used for producing 1,3-PD and D-LAC through fed-batch fermentation.

(1) Strain selection: *Escherichia coli* K12 was selected.
(2) Gene engineering modification: an exogenous 1,3-PD synthesis pathway was introduced into K12.

A glycerol dehydratase coding gene dhaB and a 1,3-PD oxidoreductase coding gene in a 1,3-PD synthesis pathway in *Klebsiella oxytoca* were selected, PCR cloning was performed, then linking to a plasmid DNA pet-Duet was performed and transformation to *Escherichia coli* K12 was performed. This bacterium was determined as K12-dhaBdhaT.

(3) Gene engineering modification: an exogenous D-LAC synthesis pathway was introduced into K12-dhaBdhaT.

A gene dldh$_{Bc}$ coding D-lactate dehydrogenase from *Bacillus coagulans* 2-6 was selected, codon optimization applicable to expression of *Escherichia coli* was performed, and the D-lactate dehydrogenase was replaced into a position of D-lactate dehydrogenase in a genome of the *Escherichia coli* K12 by using a shuttle plasmid, so as to realize constitutive expression of dldh$_{Bc}$ on the genome of the *Escherichia coli*. This bacterium was determined as K12-dhaBdhaTdldh$_{Bc}$.

(4) Seed culture: the strain in the step (3) was selected and inoculated into a glycerol culture medium under an aseptic condition and culture was performed for 15 h at 37° C. and shaker speed of 200 rpm to obtain seed culture solution.

(5) Fermentation: the seed culture solution obtained in the step (4) was inoculated into a fermentation tank containing a glycerol culture medium, an inoculation amount was 5% (v/v), fermentation temperature was 37° C., aeration speed was 0.5 vvm and stirring speed was 200 rpm, sodium hydroxide aqueous solution was used as a neutralizer for regulating pH of fermentation solution to 7.0 during fermentation, the fermentation mode was batch fermentation, and when glycerol in the glycerol culture medium was used up, fermentation was stopped.

Herein, a formula of the glycerol culture medium was as follows: 10 mM ammonium sulfate, 50 mM MOPS/KOH buffer solution with pH 7.5, 5 mM potassium phosphate buffer solution with pH 7.5, 2 mM magnesium chloride, 0.7 mM calcium chloride, 50 uM manganese chloride, 1 uM zinc chloride, 1.72 uM copper sulfate, 2.53 uM cobalt chloride, 2.4 uM sodium molybdate, 2 uM thiamine hydrochloride, 0.8 ug/mL vitamin B12 and 50 ng/ul Ampicillin. According to the need, 60 g/L glycerol was selected as a carbon source; and sterilization was performed for 20 min at 121° C.

After fermentation for 3 h, OD of the bacterium in the culture medium was 1.0, and IPTG was added to induce synthesis of 1,3-PD. 35 h later, glycerol in the glycerol culture medium was used up, fermentation was stopped, and components and concentration in the fermentation solution were detected. Main fermentation products were 1,3-PD and D-LAC, the concentration of 1,3-PD was 14.5 g/L and the concentration of D-LAC was 17.2 g/L. Byproducts ethanol, formic acid, acetic acid and succinic acid were determined, the concentration of ethanol was 2.1 g/L, the concentration of formic acid was 0.6 g/L, the concentration of acetic acid was 4.4 g/L and the concentration of succinic acid was 0.8 g/L.

Here, *Escherichia coli* K12 is used as an example for describing that an exogenous 1,3-PD synthesis pathway and/or exogenous D-LAC synthesis pathway can be introduced into strains without a 1,3-PD synthesis pathway and/or D-LAC synthesis pathway by means of gene engineering. By combining the concept given in this embodiment with embodiments 1-8, strains capable of coproducing 1,3-PD and D-LAC at high molar conversion rates can be further obtained, and this is also included in the protective scope of the present invention.

The preferred embodiments of the present invention are described above. It shall be understood that one skilled in the art may make various modifications and variations according to the concept of the present invention without contributing any inventive labor. Therefore, all technical solutions obtained by one skilled in the art according to the concept of the present invention on the basis of the prior art through logical analysis, reasoning or limited experiments shall be included in the protective scope determined by the claims.

The invention claimed is:

1. An artificial bacterium, wherein the artificial bacterium is *Klebsiella oxytoca* PDL-0 with genes budA and budB defects, or the artificial bacterium is *Klebsiella oxytoca* PDL-0 with genes budA, budB and adhE defects; or the artificial bacterium is *Klebsiella oxytoca* PDL-0 with genes budA, budB, adhE and ackA-pta defects; or the artificial bacterium is *Klebsiella oxytoca* PDL-0 with genes budA, budB, adhE, ackA-pta and poxB defects; or the artificial bacterium is *Klebsiella oxytoca* PDL-0 with genes budA, budB, adhE, ackA-pta, poxB and frdA defects, and wherein the *Klebsiella oxytoca* PDL-0 was collected in China Center for Type Culture Collection on Apr. 8, 2016, and the collection registration number is CCTCC M 2016184.

2. The artificial bacterium according to claim 1, wherein a DNA sequence of the budA is shown in SEQ ID NO:1; and/or a DNA sequence of the budB is shown in SEQ ID NO:2; and/or a DNA sequence of the adhE is shown in SEQ ID NO:3; and/or a DNA sequence of the ackA-pta is shown in SEQ ID NO:4; and/or a DNA sequence of the poxB is shown in SEQ ID NO:5; and/or a DNA sequence of the frdA is shown in SEQ ID NO:6.

3. The artificial bacterium according to claim 1, wherein the artificial bacterium has a property of coproducing 1,3-propanediol and D-lactic acid and in products obtained through coproduction, a total conversion rate of 1,3-propanediol and D-lactic acid exceeds 90%.

4. The artificial bacterium according to claim 1, wherein the artificial bacterium has the following metabolic pathways:
1) glycerol→1,3-propanediol; and
2) glycerol→pyruvic acid→D-lactic acid.

\* \* \* \* \*

SEQUENCE LISTING

<160> NUMBER OF SEQ ID NOS: 31

<210> SEQ ID NO 1
<211> LENGTH: 780
<212> TYPE: DNA
<213> ORGANISM: Klebsiella oxytoca

<400> SEQUENCE: 1

```
atgaaccatt ctgctgaatg ctcttgcgaa gagagcctgt gtgaaactct acgaggattt      60
tccgcgcaac atcccgatag cgtcatctac cagacttctc tgatgagcgc gctgttgagc     120
ggcgtttatg agggcaatac caccatcgcc gatttgctca cccacggcga tttcggcctg     180 ggcacctta atgaactgga cggcgagctg atcgcgttta gcagcgaggt ttaccagctg     240
cgcgccgacg gcagcgcccg taaagcccga atggaacagc gcacgccctt cgcggtgatg     300 acctggttc agccgcagta ccgcaaaacg tttgataaac cggtcagccg cgaacagctg     360
cacgacatta tcgaccggca aatcccctcc gataatctgt tctgcgccct gcgtatcaac     420 ggccatttc accacgccca tacccgcacc gtaccgcgcc agacgccgcc ctaccgggcg     480
atgaccgacg tgctcgacga ccagcccgtt ttccgcttca accagcgcga aggggtgctg     540
gtggggtttc gcacgccgca gcatatgcag ggcattaacg ttgccggcta ccacgaacac     600
ttcatcaccg atgaccgcca gggcggcggc catctgctcg attatcagct cgaccacggc     660
```

```
gtgctgacct tggtgagat ccacaaattg atgattgacc ttcctgccga tagcgccttc      720
ctgcaggcgg atctgcatcc tgacaatctt gatgccgcca ttcgctcagt cgaaaactaa      780
```

<210> SEQ ID NO 2
<211> LENGTH: 1680
<212> TYPE: DNA
<213> ORGANISM: Klebsiella oxytoca

<400> SEQUENCE: 2

```
gtggataatc aacatcaacc gcgccagtgg gcacacggcg ccgaccttat cgtcagccag       60
cttgaggcgc agggcgtaca acaggtgttc ggcattccag gggccaaaat cgataaagtc      120
ttcgattcgc tgctggactc ctccattcgc attattccgg tacgccacga agccaacgcc      180
gcgtttatgg ccgccgcggt tggccgcatc accgggaaag cgggcgtcgc gctggtcacg      240
tccggccccg gctgctctaa cctgattacc ggcatggcca ccgcaaacag cgaaggcgac      300
ccggtggtgg cgctgggcgg tgcggtaaaa cgcgccgaca aggccaaaca ggtgcaccag      360
agtatggata cggtggcgat gtttagtccg gtaaccaaat actcggtgga agtcaccgcc      420
gcggaagcgc tggcggaagt ggtttccaac gcgtttcgcg cagccgagca gggacgcccc      480
ggcagcgcct tcgtcagcct gccgcaggac gtggtcgacg gccggtcca cgccagggtt       540 ctgcccgcca gcgatgcgcc gcagaccggc gcggcgccgg acgaagccat tgagcgagtc      600
gcgaagatga ttgccagcgc taaaaatccg atattcctgc tcggcctgat ggccagccag      660
gcggaaaaca gcgcggcgct gcgtgaattg ctgaaaaaaa gccatatccc ggttaccagc      720
acctatcagg ccgccggcgc ggtgaatcag gaccacttta cccgcttcgc cgggcgggtt      780
gggctgttca ataaccaggc gggggatcga ctcctgcatc tcgccgacct ggtcatctgc      840
atcggctata gcccggtgga gtacgaaccg gccatgtgga ataacggcaa cgccacgctg      900
gtgcatatcg acgtactgcc ggcttacgaa gagcgcaact ataccccgga catcgagctg      960
gtcggcaata ttgccgccac cctgaacaaa ctctctcagc gtatcgacca ccagctggtg     1020
ctgtcgccgc aggccgccga gatcctggtt gaccgccagc atcagcggga gctgctcgac     1080
cgccgcggcg cgcagctgaa ccagtttgcc cttcatccgc tgcgcatcgt tcgcgccatg     1140
caggacatcg tcaacagcga cgtgacgctg accgtcgata tggggagctt tcatatttgg     1200
atcgcccgct atctctacag cttccgcgcc cgtcaggtca tgatttccaa cggccagcag     1260
accatggggg tggcgctgcc gtgggcgatt ggcgcctggc tggtcaatcc gcagcgcaaa     1320
gtggtttcgg tttccggcga cggcggcttc ctgcaatcca gtatgagct ggagaccgcc      1380 gtacggctaa aagctaacgt cctgcatatc atctgggtcg ataacggcta caacatggtg     1440
gcgattcagg aagagaaaaa ataccagcgg ctctccggcg ttgagttcgg tccggtggac     1500
tttaaagcct acgccgaagc cttcggcgcc aaagggtttg cggttgagag cgctgccgcc     1560
cttgagccga cgctgcgggc ggcgatggac gtcgacggcc ccgccgtggt cgccatcccc     1620
gttgattaca gcgacaaccc gctgctgatg ggccagcttc atctcagtca aatactttga     1680
```

<210> SEQ ID NO 3
<211> LENGTH: 2676
<212> TYPE: DNA
<213> ORGANISM: Klebsiella oxytoca

<400> SEQUENCE: 3

```
atggctgtta ctaatgtcgc tgaacttaac gcactcgtcg agcgcgtaaa aaaagcccag      60
cgtgaatatg ccagtttcac tcaagaacaa gtagacaaaa tcttccgcgc cgccgctctg     120
gccgctgcag atgctcgaat ccctctcgcc aagatggccg ttgccgaatc cggcatgggc     180
atcgtcgaag ataaagtgat caaaaaccac tttgcttccg aatacattta taacgcctat     240
aaagatgaaa agacctgcgg cgtcctgtct gaagatgaca ccttcggtac catcaccatc     300
gctgagccga ttggtattat ctgcggtatc gtcccgacca ctaacccaac ttcaaccgct     360
atctttaaat ctctgattag cctgaagacc cgtaacgcca tcatcttctc tccgcatccg     420
cgtgctaaag atgcgaccaa caaagcggct gatatcgtac tgcaggcagc tatcgcagcc     480
ggtgcgccga agatctgat tggttggatt gaccagcctt ccgttgaact gtcaaatgcg     540
ctgatgcacc atccggatat caacctgatc cttgcgaccg gcggtccggg catggttaag     600
gcggcgtaca gctccggtaa acctgccatc ggcgtaggcg caggtaacac gcctgttgtt     660
atcgatgaaa cggctgatat caagcgtgcc gttgcttccg tcctgatgtc taaaaccttc     720
gataacggcg ttatctgtgc ttctgagcaa tccgttgtgg ttgtagattc cgtatacgat     780
gccgttcgcg aacgtttctc cagccacggc ggctatctgc tgcagggcca ggagctgaag     840
gctgttcaga atatcatcct gaaaaacggc gccctgaacg ccgcgatcgt aggtcaaccg     900
gcgtataaaa tcgctgaact ggccggcttc accgtccctg tttccaccaa aattctgatt     960
ggtgaagtca ccgacgttga tgaaagcgaa ccgtttgccc acgaaaaact gtctccgacg    1020
ctggcaatgt accgtgcgaa gaacttcgaa gacgcggttg ataaagctga aaaactggtg    1080
gcaatgggcg gtatcggtca tacctcttgc ctgtataccg accaggacaa ccagccagaa    1140
cgcgttgctt acttcggtca gctgatgaaa accgcacgta tcctgatcaa caccccctgct    1200
tctcagggtg gtatcggtga cctgtacaac ttcaaactcg caccttccct gactctgggt    1260
tgtggttcat ggggtggtaa ctccatctct gaaaacgttg gtcctaagca cctgatcaac    1320
aagaaaaccg ttgctaagcg agctgaaaac atgttgtggc acaaacttcc gaaatctatc    1380
tacttccgtc gtggctcact gccaatcgcg ctggatgaag tgattactga tggtcacaaa    1440
cgcgcgctga tcgtgaccga ccgcttcctg ttcaacaacg gctatgctga ccagatcacc    1500
tctgtgctga aagcggctgg cgttgaaacc gaagttttct tgaagtgga agctgacccg    1560
acgctgacca tcgttcgtaa aggcgctgag ctggcgaact ccttcaaacc agacgtgatt    1620
atcgcgctgg gcggcggttc cccgatggat gcggcgaaaa tcatgtgggt tatgtacgag    1680
caccccggaaa cccacttcga agaactggcg ctgcgcttta tggatatccg taaacgtatc    1740
tacaagttcc cgaaaatggg cgtgaaagcc aaaatggtcg ccatcaccac gacttccggt    1800
accggttctg aagttacgcc gttcgccgtt gttaccgatg atgcaaccgg tcagaaatac    1860
ccgctggcag actatgccct gactccggat atggcgattt tgatgccaa cctggtcatg    1920
gaaatgccga gtcactgtg tgctttcggt ggtctggatg cggtgactca tgccctggaa    1980
gcttacgttt ccgtactggc ttccgagttc tctgacggcc aggcgctgca ggctctgaaa    2040
ctgctgaaag aaaacctgcc agcgtcctac cacgaaggtt ctaagaaccc ggtagcgcgt    2100
gagcgtgtgc acagtgctgc gaccatcgcc ggtatcgcgt ttgcgaacgc cttcctcggg    2160
gtatgtcact caatggcgca caagctgggc tctcagttcc acattcctca cggtctggcg    2220
aacgccctgc tgatcagcaa cgttattcgc tataacgcta acgacaaccc gactaaacag    2280
```

| | |
|---|---:|
| acagcattca gccagtacga ccgcccgcag gcacgtcgtc gctacgctga aatcgcggac | 2340 |
| catctgggtc tgactgcacc gggtgaccgt accgcagcga aaatcgaaaa actgcttggc | 2400 |
| tggttggacg aaatcaaagc tgagctgggt attcctaagt ctatccgcga agctggcgtg | 2460 |
| caggaagctg atttcctggc ccacgttgac aagctgtctg aagacgcatt tgacgaccag | 2520 |
| tgcaccggcg ctaacccgcg ctacccgctg atcgctgagc tgaaacagat tctgctggat | 2580 |
| acgttctacg gacgtaatta cgttgaaggc agcgtggaag agaaaaaaga agtcgcgccg | 2640 |
| gctaaagctg agaagaaagc gaaaaaatcc gcttaa | 2676 |

<210> SEQ ID NO 4
<211> LENGTH: 3549
<212> TYPE: DNA
<213> ORGANISM: Klebsiella oxytoca

<400> SEQUENCE: 4

| | |
|---|---:|
| atgtcgagta agttagtact ggttctgaac tgcggtagct cctctctgaa attcgctatc | 60 |
| cttgatgccg tcaacggcga cgaataccctg tccggtttag cagaatgttt ccatcttcct | 120 |
| gaagcccgta tcaaatggaa aatggacggc agcaagcaag aagccgaatt aggcgctggc | 180 |
| gctgctcaca gtgaagcgct gaactttatc gttaacacta ttctggcaca aaaaccagaa | 240 |
| ctgtctgctc agctgaccgc aatcggccac cgcatcgttc acggtggtga aaaatacacc | 300 |
| agctccgtcg ttatcgatga ctccgtgatt cagggaatca agactccgc ctctttcgct | 360 |
| ccgctgcaca accccggcgca cctgatcggt atcgctgagg cgctgaaatc tttccctaat | 420 |
| ctgaaagaca agaacgttgc cgtgttcgac accgcgttcc atcagaccat gccggaagaa | 480 |
| tcttacctct atgccctgcc gtacagcctg tataaagaac acggcgtacg tcgctacggc | 540 |
| gcgcacggca ccagccacta ctatgtgact caggaagccg cgaaagttct gaacaaaccg | 600 |
| gttgaagaac tgaacatcat cacctgccat ctgggcaacg tggttccgt ttccgctatc | 660 |
| cgcaacggta aatgcgttga cacttccatg gggctgactc cactggaagg tctggttatg | 720 |
| ggtacgcgtt ctggcgatat cgacccggca atcattttcc atctgcacga tgccctgggc | 780 |
| atgagcgtag acgccatcaa caaaatgctg accaaagagt ccggtctgct cggtctgacc | 840 |
| gaagtgacca gcgactgccg ctacgttgaa gacaactacc aggaaaaagc tgacgctaaa | 900 |
| cgtgccatgg acgtttactg ccaccgcctg gcgaaatata tcggctccta caccgcgctg | 960 |
| atggacggtc gtctggacgc cgtcgtattc accggtggta tcggtgagaa cgccgcgatg | 1020 |
| gttcgcgaac tgtctctggg caaactgggc gtactgggct ttgaagttga tcacgagcgt | 1080 |
| aacctggcag cccgtttcgg caagtctggc ttcatcaaca agaaggcac tcgcccggct | 1140 |
| atcgtcattc cgaccaacga agagctggtc atcgcgcaag acgccaaccg tctgaccgcc | 1200 |
| tgattccaca ccgccagcca taaccctaaa taattcgagt tgcaggaagg cggcgacgca | 1260 |
| gagaatcccc caggagcgta cgagtagtac gtaactgggg tgagcgagta aagccaacgc | 1320 |
| acatgcaact tgaagtatga cgggaagctg gtggtgcagt tttgtatccc gcctgatact | 1380 |
| ggcggtaacg aaagaggata tatcgtgtcc cgtacaatca tgctgatccc taccggaacc | 1440 |
| agcgtaggcc tgaccagcgt cagcctcggt gttatccgtg ctatggaacg taaaggcgtt | 1500 |
| cgtctgagcg tctttaaacc tatcgctcaa ccgcgtgccg gtggcgatgc gccagaccag | 1560 |
| actaccacta ttattcgcgc gaactccgac cttccggccg cagaaccgct gaagatgagc | 1620 |
| cacgttgagt cgctgctctc cagcaaccag aaagacgtgc tgatggaaga gatcatcgcc | 1680 |
| aactaccacg ccaacgctca ggatgcggaa gtggtgctgg ttgaaggtct ggtcccgacc | 1740 |

```
cgcaaacatc agtttgccca gtctctgaac tacgaaatcg cgaaaacgct gaacgctgaa      1800 atcgttttg tgatgtccca gggtaccgat actcctgaac agctgaaaga gcgcattgag       1860
ctgactcgca gcagcttcgg cggcgcgaaa aacaccagcg tcaccggcgt gatcgtcaac      1920
aagctgaatg cgccggttga cgaacagggc cgtactcgcc ctgacctgtc ggaaatcttc      1980
gacgactctt ccaaagcaaa agtcgtgaag atcgatccgg ctcagctgca gagcggtagc     2040
ccattaccgg ttctgggcgc ggtgccgtgg agcttcgatc tgatcgccac ccgcgcgatt     2100
gatatggcgc atcacctgaa cgccaccatc atcaacgaag gcgacatcaa tacccgtcgc     2160
gtgaagtccg tcaccttctg tgcgcgtagc attccgcaca tgctggaaca cttccgcgca     2220
ggctccctgc tggtcacttc cgcagaccgt cctgacgttc tggtcgccgc ctgcctggcc     2280
gcgatgaacg cgtggaaaat cggcgctatc ctgctgaccg gcggctacga aatggacgcc     2340
cgcatcagca aactgtgcga acgcgcgttt gcaaccggcc tgccggtatt catggttaac     2400
accaacacct ggcagacctc tctgagcctg cagagcttca acctggaagt tccggttgac     2460
gatcacgagc gcatcgagaa agttcaggaa tacgtggcta actatatcaa cgccgactgg     2520
attgaatcgc tgaccgcaac ttccgagcgc agccgtcgcc tctctccgcc agccttccgc     2580
tatcagctta ccgagctggc gcgtaaagca ggcaagcgcg tcgtgctgcc ggaaggcaac     2640
gagccgcgta ccgttaaagc cgcggctatc tgcgccgagc gcggtatcgc cacctgcgta     2700
ctgctgggta acccggatga aatcacccgc gtggccgcct ctcagggcgt agagctgggc     2760
gccggtattg aaatcgttga cccggaagtg gttcgcgaaa gctacgttgc tcgcctggtc     2820
gagctgcgta agagcaaggg gatgaccgaa gcggttgccc gcgagcagct ggaagacaac     2880
gtggttctcg gcaccctgat gctcgagcag gacgaagtcg acggcctggt atccggcgcg     2940
gttcacacca ccgccaacac catccgtccg ccgctgcagc tgatcaaaac tgcgccgggc     3000
agctctctgg tctcctccgt attcttcatg ctgctgccgg aacaggttta cgtttacggc     3060
gactgcgcga tcaacccgga tccgaccgct gaacagctgg ctgaaatcgc catccagtcc     3120
gcagactccg caattgcctt cggcatcgaa ccgcgcgtgg ccatgctctc ctactccacc     3180
ggcacctccg gcgccggcag cgatgtagag aaagtacgcg aagcgacccg tctggcgcag     3240
gaaaaacgtc ctgacctgat gatcgacggc ccgctgcagt acgatgcggc ggtcatggct     3300
gacgttgcga aatccaaagc gccgaactcc ccggttgccg ccgcgctac cgtgtttatc     3360 ttcccggatc tgaacaccgg taacaccact tacaaagccg tacagcgttc tgccgacctg     3420
atctccatcg gccgatgct gcaggggatg cgtaagccgg tgaacgacct gtcccgtggc     3480
gcgctggttg acgatatcgt ctataccatc gccctgaccg cgattcagtc gtcccagcag     3540
caagcataa                                                             3549
```

<210> SEQ ID NO 5
<211> LENGTH: 1719
<212> TYPE: DNA
<213> ORGANISM: Klebsiella oxytoca

<400> SEQUENCE: 5

```
atgaaacaga ccgtggcggc atacattgcc aaaactcttg aacaggctgg cgttaaacgt       60
atttggggcg taaccgggga ttcgctcaac ggcttaagcg acagcctgaa ccgtatgggg     120
accatcgact ggatgcccac cgccatgaa gaagtggccg ccttcgccgc cggggcggaa      180
gcgcagctta ccggcgaact ggcggtctgc gcaggctcct gcgggccggg caacctgcat     240
```

```
ctgattaacg gccttttcga ctgccaccgc aatcacgttc cggttctggc catcgccgcc    300
catattcctt ccagcgaaat cggcagcggc tattttcagg aaacgcatcc acaggagcta    360
ttccgggaat gcagtcacta ctgtgaactg gtctcaaccc cggaacagat cccgcaggtg    420
ctggccatcg ccatgcgcaa agcggtgatt aaccgcggcg tctcggtagt ggtgcttccc    480
ggcgacgttg cgctgaaagc cgcgccggaa agcgccagca gccactggta ccacgcaccg    540
ctgccgcagg tgacgccggc ggaagaagag ctgaaaaagc tggcccagct gctgcgctat    600
tcaagcaaca tcgccctgat gtgcggcagc ggctgcgccg ggcgcataa agagctggta    660
gacttcgccg cgaagctcaa agcgcctatc gttcacgcgc tgcgcggcaa agagcacgta    720
gaatacgaca cccttatga tgtggggatg accggactga ttggcttctc ctccggcttc    780
cacaccatga tgaacgccga caccctggtg ctgctcggca cccagttccc ctatcgcgct    840
ttctacccga cggacgcgaa aatcattcag attgatatca atcccggcag tattggcgcc    900
cacagtaaag tggatatggc gctggtcggc gatattaaat cgaccctcag cgcgctgatg    960
ccgcatcttg aggagaaaac cgaccgtaag ttcctcgata aagcgctgga acactatcgc   1020
gacgcgcgca aggggcttga tgacctggca agcccagcg aaaaaacaat tcatccgcag   1080
tatctggcgc agcgcatcag ccactatgcc gacgacgatg ccatctttac ctgtgacgtg   1140
ggtacgccga ccgtctgggc cgcgcgctat ttgcagatga acggtaagcg ccgcctgctc   1200
ggatcgttca atcatgggtc aatggctaac gccatgccgc aggccatcgg tgcgaaggcc   1260
accgcccctg accgtcaggt tgtggcaatg tgcggcgacg gcggcttcag catgctgatg   1320
ggggattttc tctcgctggc gcagatgaag ctgccggtga agatcgttat cttcaataac   1380
agcgtcctgg gcttcgtggc gatggagatg aaggccgggg gctatctgac agacggcact   1440
gaacttcacg ccaccaactt tgcccgcatc gccgaagcgt gcggcattaa gggcatacgt   1500
gttgaaagcg cgtcagaggt tgatgaagcg ctgcaaaccg ctttcgctac cgatggtccg   1560
gtcctggtgg atgtggtcgt cgccagtgaa gagctggcga tgccgccgca aattaaactg   1620
gagcaggcca aaggtttcag cctttatatg ctgcgcgcga ttatcagcgg ccgcggcgac   1680
gaagttatcg aactggcgaa aactaactgg ctaaggtaa                         1719

<210> SEQ ID NO 6
<211> LENGTH: 1791
<212> TYPE: DNA
<213> ORGANISM: Klebsiella oxytoca

<400> SEQUENCE: 6
gtgcaaactt ttcaagccga tcttgccgta ataggcgcag gcggagcagg tcttcgcgcc     60
gcaatagccg ccgcgcaagc taatccaaat gcaaaaatcg ctctaatttc aaaagtctat    120
cctatgcgca gccataccgt tgctgctgaa gggggttccg ctgccgtcgc gcaggatcat    180
gatagcttcg agtaccattt tcacgacacc gttgccggcg cgactggct atgtgagcag    240
gacgtcgttg actacttcgt tcatcactgc ccgacggaaa tgacccagct cgaacagtgg    300
ggatgcccgt ggagccgccg cccggacggc agcgtcaacg tccggcgatt cggcggcatg    360
aagatcgaac gaacctggtt cgctgccgat aaaaccggct tcatatgct gcacaccctg    420
ttccagacct cgcttcaatt cccgcaaatc caacgcttcg acgaacattt tgttctggat    480
attctggtcg atgatgggca ggctcgcggt ctggtcgcga tgaatatgat ggaaggtacg    540
ctggtgcaga tccgcgccaa cgcggtagtt ctggctaccg cggcgctgg acgcgtgtat    600
cgctacaata ccaacggcgg tatcgtcacc ggcgacggga tgggtatggc gctcagccac    660
```

```
ggcgtaccgc tgcgcgatat ggagttcgtg cagtaccacc ccaccggcct gccgggctcc    720
ggtattctga tgacggaagg ctgccgcggc gaaggcggta ttctggtcaa caagaacggc    780
taccgctacc tgcaggatta cggcatgggt ccggaaacac cgctgggcga accgaaaaat    840
aaatatatgg agctgggtcc gcgcgataaa gtctcccagg ctttctggca cgaatggcgc    900
aagggcaaca cgatccctac gccgcgaggc gatgtggtct atctcgatct gcgccatttg    960
ggtgagaaaa agctgcttga acgtctgccg tttatctgtg aactctcgaa agcctacgtt   1020
ggcgtcgatc cggtaaaaga gccgattccg gtgcgtccaa ccgcacacta ccaccatggc   1080
gggattgaaa ccgaccagca gtgtgaaacc cgtatcaaag gctgtttgc cgttggcgaa    1140
tgttcttctg tgggtctgca cggcgccaac cgccttggct ccaactccct ggcggagctg   1200
gtggtctttg gtcgtctggc cggtgagcag gccatgcagc gcgcaaccga agcgggcgaa   1260
gccaatagcg ccgcgctgga cgcgcaggtc gtcgatatcg agaagcgcct gaaagacctg   1320
gttaatcagg aaggtaacga gaactgggcg aagattcgcg acgacatggg tctgtcgatg   1380
gaagaaggct gcggcatcta ccgtacgccg gagctcatgc agaaaacggt cgataagctc   1440
gccgagctgc aggagcgctt caagcgcgtg cggatcaccg acacgtccag cgtgttcaat   1500
accgacctgc tgtacaccat cgagctgggc catggcctga acgtcgccga atgtatggcg   1560
cattccgccc tcgcgcgtaa agagtcccgc ggcgcgcatc agcgcctgga tgaaggctgc   1620
accgagcgcg acgacgtcaa cttcctcaag catacccctcg ccttcgcga tgccgatggt    1680
cacaccaggc tggagtacag tgatgtgaaa atcaccactc tgccgccggc aaaacgcgtg   1740
tacggtgcgg aagcggaagc agccgagaag aaggagacga cgaatggctg a            1791
```

<210> SEQ ID NO 7  
<211> LENGTH: 1410  
<212> TYPE: DNA  
<213> ORGANISM: Klebsiella oxytoca

<400> SEQUENCE: 7

```
ggtagcgccc tcccgaaggt taagctacct acttcttttg caacccactc ccatggtgtg     60
acgggcggtg tgtacaaggc ccgggaacgt attcaccgtg gcattctgat ccacgattac    120
tagcgattcc gacttcatgg agtcgagttg cagactccaa tccggactac gacatacttt    180
atgaggtccg cttgctctcg cgaggtcgct tctctttgta tatgccattg tagcacgtgt    240
gtagccctac tcgtaagggc catgatgact tgacgtcatc cccaccttcc tccagtttat    300
cactggcagt ctcctttgag ttcccgaccg aatcgctggc aacaaaggat aagggttgcg    360
ctcgttgcgg gacttaaccc aacatttcac aacacgagct gacgacagcc atgcagcacc    420
tgtctcagag ttcccgaagg caccaaagca tctctgctaa gttctctgga tgtcaagagt    480
aggtaaggtt cttcgcgttg catcgaatta aaccacatgc tccaccgctt gtgcgggccc    540
ccgtcaattc atttgagttt taaccttgcg gccgtactcc ccaggcggtc gacttaacgc    600
gttagctccg gaagccactc ctcaagggaa caacctccaa gtcgacatcg tttacagcgt    660
ggactaccag ggtatctaat cctgtttgct ccccacgctt tcgcacctga gcgtcagtct    720
ttgtccaggg ggccgccttc gccaccggta ttcctccaga tctctacgca tttcaccgct   780
acacctggaa ttctaccccc ctctacaaga ctccagcctg ccagtttcga atgcagttcc    840
caggttgagc ccggggattt cacatccgac ttgacagacc gcctgcgtgc ctttacgcc    900
cagtaattcc gattaacgct tgcaccctcc gtattaccgc ggctgctggc acggagttag   960
```

```
ccggtgcttc ttctgcgggt aacgtcaatc gacaaggtta ttaaccttat caccttcctc    1020
cccgctgaaa gtactttaca acccgaaggc cttcttcata cacgcggcat ggctgcatca    1080
ggcttgcgcc cattgtgcaa tattccccac tgctgcctcc cgtaggagtc tggaccgtgt    1140
ctcagttcca gtgtggctgg tcatcctctc agaccagcta gggatcgtcg cctaggtgag    1200
ccgttacccc acctactagc taatcccatc tgggcacatc tgatggcaag aggcccgaag    1260 gtcccctct ttggtcttgc gacgttatgc ggtattagct accgtttcca gtagttatcc     1320
ccctccatca ggcagtttcc cagacattac tcacccgtcc gccactcgtc acccgagagc    1380
aagctctctg tgctaccgtt cgactgcatg                                     1410
```

<210> SEQ ID NO 8
<211> LENGTH: 36
<212> TYPE: DNA
<213> ORGANISM: Artificial Sequence
<220> FEATURE:
<223> OTHER INFORMATION: Synthetic Construct

<400> SEQUENCE: 8

```
acatgattac gaattcatga accattctgc tgaatg                                36
```

<210> SEQ ID NO 9
<211> LENGTH: 30
<212> TYPE: DNA
<213> ORGANISM: Artificial Sequence
<220> FEATURE:
<223> OTHER INFORMATION: Synthetic Construct

<400> SEQUENCE: 9

```
aacgggctgg catcaccgcg aagggcgtgc                                      30
```

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10

```
cgcggtgatg ccagcccgtt ttccgcttca                                      30
```

<210> SEQ ID NO 11
<211> LENGTH: 36
<212> TYPE: DNA
<213> ORGANISM: Artificial Sequence
<220> FEATURE:
<223> OTHER INFORMATION: Synthetic Construct

<400> SEQUENCE: 11

```
taccgagctc gaattcttag ttttcgactg agcgaa                               36
```

<210> SEQ ID NO 12
<211> LENGTH: 35
<212> TYPE: DNA
<213> ORGANISM: Artificial Sequence
<220> FEATURE:
<223> OTHER INFORMATION: Synthetic Construct

<400> SEQUENCE: 12

```
acgcgaattc gtggataatc aacatcaacc gcgcc                                35
```

<210> SEQ ID NO 13
<211> LENGTH: 28

<212> TYPE: DNA
<213> ORGANISM: Artificial Sequence
<220> FEATURE:
<223> OTHER INFORMATION: Synthetic Construct

<400> SEQUENCE: 13
acgcggatcc ggggcgtccc tgctcggc                                          28

<210> SEQ ID NO 14
<211> LENGTH: 35
<212> TYPE: DNA
<213> ORGANISM: Artificial Sequence
<220> FEATURE:
<223> OTHER INFORMATION: Synthetic Construct

<400> SEQUENCE: 14
acgcggatcc atcgcccgct atctctacag cttcc                                  35

<210> SEQ ID NO 15
<211> LENGTH: 35
<212> TYPE: DNA
<213> ORGANISM: Artificial Sequence
<220> FEATURE:
<223> OTHER INFORMATION: Synthetic Construct

<400> SEQUENCE: 15
acgcctgcag atttgactga gatgaagctg gccca                                  35

<210> SEQ ID NO 16
<211> LENGTH: 36
<212> TYPE: DNA
<213> ORGANISM: Artificial Sequence
<220> FEATURE:
<223> OTHER INFORMATION: Synthetic Construct

<400> SEQUENCE: 16
acatgattac gaattcatgg ctgttactaa tgtcgc                                 36

<210> SEQ ID NO 17
<211> LENGTH: 30
<212> TYPE: DNA
<213> ORGANISM: Artificial Sequence
<220> FEATURE:
<223> OTHER INFORMATION: Synthetic Construct

<400> SEQUENCE: 17
tgctgtctgt tggcgttacg ggtcttcagg                                        30

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
cgtaacgcca acagacagca ttcagccagt                                        30

<210> SEQ ID NO 19
<211> LENGTH: 36
<212> TYPE: DNA
<213> ORGANISM: Artificial Sequence
<220> FEATURE:
<223> OTHER INFORMATION: Synthetic Construct

<400> SEQUENCE: 19
taccgagctc gaattcttaa gcggattttt tcgctt        36

<210> SEQ ID NO 20
<211> LENGTH: 36
<212> TYPE: DNA
<213> ORGANISM: Artificial Sequence
<220> FEATURE:
<223> OTHER INFORMATION: Synthetic Construct

<400> SEQUENCE: 20
acatgattac gaattcatgt cgagtaagtt agtact        36

<210> SEQ ID NO 21
<211> LENGTH: 30
<212> TYPE: DNA
<213> ORGANISM: Artificial Sequence
<220> FEATURE:
<223> OTHER INFORMATION: Synthetic Construct

<400> SEQUENCE: 21
cacgcgcggt cctcagcgat accgatcagg        30

<210> SEQ ID NO 22
<211> LENGTH: 30
<212> TYPE: DNA
<213> ORGANISM: Artificial Sequence
<220> FEATURE:
<223> OTHER INFORMATION: Synthetic Construct

<400> SEQUENCE: 22
atcgctgagg accgcgcgtg gccatgctct        30

<210> SEQ ID NO 23
<211> LENGTH: 36
<212> TYPE: DNA
<213> ORGANISM: Artificial Sequence
<220> FEATURE:
<223> OTHER INFORMATION: Synthetic Construct

<400> SEQUENCE: 23
taccgagctc gaattcttat gcttgctgct gggacg        36

<210> SEQ ID NO 24
<211> LENGTH: 36
<212> TYPE: DNA
<213> ORGANISM: Artificial Sequence
<220> FEATURE:
<223> OTHER INFORMATION: Synthetic Construct

<400> SEQUENCE: 24
acatgattac gaattcatga aacagaccgt ggcggc        36

<210> SEQ ID NO 25
<211> LENGTH: 30
<212> TYPE: DNA
<213> ORGANISM: Artificial Sequence
<220> FEATURE:
<223> OTHER INFORMATION: Synthetic Construct

<400> SEQUENCE: 25
aaaatccccc gggttgagac cagttcacag                                              30

<210> SEQ ID NO 26
<211> LENGTH: 30
<212> TYPE: DNA
<213> ORGANISM: Artificial Sequence
<220> FEATURE:
<223> OTHER INFORMATION: Synthetic Construct

<400> SEQUENCE: 26
gtctcaaccc ggggattttt ctctcgctgg                                              30

<210> SEQ ID NO 27
<211> LENGTH: 36
<212> TYPE: DNA
<213> ORGANISM: Artificial Sequence
<220> FEATURE:
<223> OTHER INFORMATION: Synthetic Construct

<400> SEQUENCE: 27
taccgagctc gaattcttac cttagccagt tagttt                                       36

<210> SEQ ID NO 28
<211> LENGTH: 36
<212> TYPE: DNA
<213> ORGANISM: Artificial Sequence
<220> FEATURE:
<223> OTHER INFORMATION: Synthetic Construct

<400> SEQUENCE: 28
acatgattac gaattcgtgc aaacttttca agccga                                       36

<210> SEQ ID NO 29
<211> LENGTH: 30
<212> TYPE: DNA
<213> ORGANISM: Artificial Sequence
<220> FEATURE:
<223> OTHER INFORMATION: Synthetic Construct

<400> SEQUENCE: 29
gtagatgccg agccggtttt atcggcagcg                                              30

<210> SEQ ID NO 30
<211> LENGTH: 30
<212> TYPE: DNA
<213> ORGANISM: Artificial Sequence
<220> FEATURE:
<223> OTHER INFORMATION: Synthetic Construct

<400> SEQUENCE: 30
aaaaccggct cggcatctac cgtacgccgg                                              30

<210> SEQ ID NO 31
<211> LENGTH: 36
<212> TYPE: DNA
<213> ORGANISM: Artificial Sequence
<220> FEATURE:
<223> OTHER INFORMATION: Synthetic Construct

<400> SEQUENCE: 31
taccgagctc gaattctcag ccattcgtcg tctcct                                       36